United States Patent [19]

Jikihara et al.

[11] 4,360,375

[45] * Nov. 23, 1982

[54] PHENOXYPHENOXY UNSATURATED DERIVATIVES AND HERBICIDAL COMPOSITION

[75] Inventors: Kazuo Jikihara, Kakegawa; Shigekazu Itoh; Shuichi Takayama, both of Shimizu; Koichi Sato; Ichiro Kimura, both of Shizuoka; Isao Chiyomaru, Shimizu, all of Japan

[73] Assignee: Kumiai Chemical Industry Co., Ltd., Tokyo, Japan

[ * ] Notice: The portion of the term of this patent subsequent to Aug. 17, 1996, has been disclaimed.

[21] Appl. No.: 219,503

[22] Filed: Dec. 23, 1980

Related U.S. Application Data

[62] Division of Ser. No. 6,387, Jan. 25, 1979, Pat. No. 4,263,040.

[30] Foreign Application Priority Data

Feb. 18, 1978 [JP] Japan .................................. 53-17785
Jul. 7, 1978 [JP] Japan .................................. 53-82732
Oct. 14, 1978 [JP] Japan ................................ 53-126592

[51] Int. Cl.³ ...................... C07C 69/76; A01N 9/24; A01N 37/06

[52] U.S. Cl. ........................... 71/88; 562/472; 560/63; 560/255; 560/228; 560/107; 560/164; 560/32; 560/62; 564/161; 564/347; 564/430; 260/439 R; 260/429.9; 260/455 R; 260/463; 260/501.1; 260/465 D; 568/637; 546/1; 71/100; 71/105; 71/108; 71/111; 71/115; 71/118; 71/121; 71/122; 71/124; 71/94; 549/501

[58] Field of Search ................. 560/63, 255, 228, 107, 560/164, 32, 62; 71/108, 100, 105, 111, 115, 118, 121, 122, 124, 94, 88; 562/472; 564/161, 347, 430; 260/439 R, 429.9, 346.22, 455 R, 463, 501.1, 465 D; 568/637; 546/1

[56] References Cited

U.S. PATENT DOCUMENTS 3,553,252 1/1971 Mine et al. .......................... 560/63
4,163,661 8/1979 Jikihara et al. ...................... 71/108
4,205,978 6/1980 Rohr et al. .......................... 71/108

Primary Examiner—Bernard Helfin
Attorney, Agent, or Firm—Oblon, Fisher, Spivak, McClelland & Maier

[57] ABSTRACT

A herbicidal composition which comprises a phenoxyphenoxy unsaturated derivative having the formula:

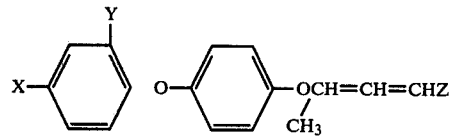

wherein X represents a halogen atom or CF₃; Y represents a hydrogen atom or a halogen atom; and Z represents —COOR, —COR″, —COOH, —CH₂OH, or —CH₂OR‴.

10 Claims, No Drawings

PHENOXYPHENOXY UNSATURATED DERIVATIVES AND HERBICIDAL COMPOSITION

This is a division of application Ser. No. 6,387, filed Jan. 25, 1979 and now U.S. Pat. No. 4,263,040.

DETAILED DESCRIPTION OF THE INVENTION

The present invention relates to phenoxyphenoxy unsaturated derivatives having the formula

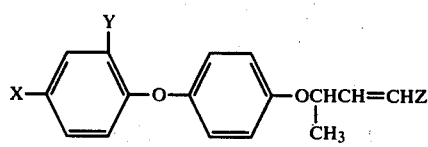

wherein X represents a halogen atom or $CF_3$; Y represents a hydrogen atom or a halogen atom; and Z represents —COOR, —COSR', —COR'', —COOH, —CH$_2$OH or —CH$_2$OR''' and R represents cyanoethyl, dialkylaminoethyl, alkoxyalkyl, benzyl, dialkylbenzyl, alkylbenzyl, halobenzyl, pyridinomethyl, furfuryl, cycloalkyl, methylcycloalkyl, phenyl, halophenyl, methyl phenyl, alkoxy alkyleneoxy alkyl, methoxymethylbutyl group, a metal atom, amino, alkylamino or arylamino group; and when X is a halogen atom, R can be an alkyl, haloalkyl, alkenyl, haloalkenyl, alkynyl or hydrogen atom group; and R' represents alkyl, phenyl, chlorophenyl, chlorobenzyl or methoxy benzyl group, and R'' represents, amino, alkylamino, dialkylamino, phenylamino or phenylamino group which may be substituted by halo or alkyl group, and R''' represents an acetyl, chloroacetyl, benzoyl, ethoxycarbonyl, methylcarbamoyl or phenylcarbamoyl group.

The present invention also relates to herbicidal compositions comprising said compound as an active ingredient.

Recently, many herbicides have been proposed and practically used to contribute for elimination of agricultural labor.

Thus, various problems on herbicidal effects and safety of the herbicides have been found in the practical applications.

It has been required to find improved herbicides which have no adverse effect to the object plants and effective to noxious weeds in a small dose of the active ingredient and significantly safe without any environmental pollution.

The inventors have synthesized various phenoxyphenoxy unsaturated derivatives so as to find satisfactory herbicides and have studied herbicidal effects thereof.

The novel compounds of phenoxyphenoxy unsaturated derivatives having the formula (I) of the present invention have superior herbicidal activity to gramineous weeds such as barnyard grass, crab grass and Johnson grass incomparison with the compounds described in Japanese Unexamined Patent Publication No. 33637/1977 such as methyl4-[4-(4 trifluoromethylphenoxy) phenoxy] crotonate, ethyl 4-[4-(4-trifluoromethyl-2-chlorophenoxy) phenoxy] crotonate, ethyl γ-[4-(4-trifluoromethylphenoxy) phenoxy] valerylate and ethyl γ-[4-(4-trifluoromethyl-2-chlorophenoxy) phenoxy] valerylate. The novel compounds of the present invention have superior residual activity in a soil treatment in comparison with α-[4-(4-trifluoromethylphenoxy) phenoxy] propionic acid derivatives disclosed in Japanese Unexamined Patent Publication No. 12924/1976.

The novel compounds of the present invention have superior herbicidal activities in comparison with dimethylammonium γ-[4-(4-chlorophenoxy) phenoxy] valerianate, and sodium γ-[4-(2',4'-dichlorophenoxy) phenoxy] valerianate disclosed in Japanese Unexamined Patent Publication No. 131540/1977; and ethyl α-[4-(4'-chlorophenoxy) phenoxy] propionate, methyl-α-[4-(2',4'-dichlorophenoxy) phenoxy] propionate, sodium α-[4-(4'-bromophenoxy) phenoxy] propionate and potassium α-[4-(4'-chlorophenoxy) phenoxy] propionate disclosed in Japanese Unexamined Patent Publication No. 54525/1974 and sodium α-[4-(2-chloro-4'-bromophenoxy) phenoxy propionate and dimethylammonium α-2'-chloro-4'-bromophenoxy phenoxy propionate, disclosed in Japanese Unexamined Patent Publication No. 89628/1977.

The novel compounds of the present invention also have excellent effects such as a long suppression of weeds in later emergence; a long suppression of recovery from an incomplete suppression of weeds in a foliage treatment; growth control of grown weeds and excellent stability to the factors for varying the activity caused by rainfall, atmospheric moisture and high temperature to impart stable activity.

The novel compounds of the present invention have methyl group at γ-position of the phenoxyphenoxy unsaturated compounds (I) whereby the special herbicidal effect especially, significant herbicidal effect to gramineous weeds such as Johnson grass, dent foxtail, barnyard grass and large crab grass can be imparted.

The novel compounds of the present invention have significant selectivity without phytotoxicity to broad leaf crop plants such as radish, soybean, peanut, cotton, flax, beet, pimento and sunflower, but completely control gramineous weeds barnyard grass, large crab grass, Johnson grass, wild sorghum, quack grass, dent foxtail and paspalum grass.

The novel compounds of the present invention can be applied as herbicides by desirable methods in every season such as the soil treatment and the foliage treatment in post-emergence and pre-emergence.

The significant characteristics of the novel compounds are to have significant herbicidal effect in the foliage treatment, for example, to completely control Johnson grass in 5 leaf-stage or more.

Typical gramineous weeds which are effectively controlled by the herbicides of the present invention are as follows: Johnson grass, quack grass, para-grass, southern sandbar, finger grass, bermuda grass, crowfoot grass, large crab grass, crab grass, barnyard grass, jungle rice, cattail grass, goose grass, cogon grass, wrinkle grass, southern cut grass, Bearded splangle top, red splangle top, mexican splangle top, brown top panicum, sour paspalum, water paspalum, natal grass, raoul grass, green foxtail, bristly foxtail, yellow foxtail.

The phenoxyphenoxy unsaturated derivatives having the formula (I) can be produced by the following processes.

(1) The phenoxyphenoxy unsaturated derivatives having the formula (I)

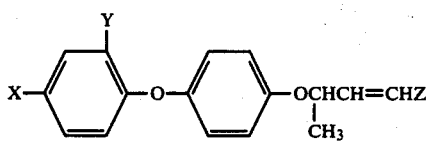    (I)

(X, Y and Z are defined above) can be produced by reacting an unsaturated halide having the formula

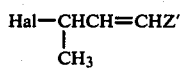    (II)

(Z' is Z defined above or a group convertible to Z and Hal is a halogen atom) with a phenoxyphenol having the formula

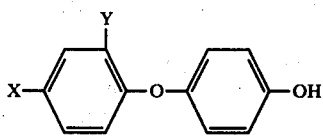    (III)

(X and Y are defined above) in the presence of a base at 0° to 150° C. for 1 to 20 hours and if necessary, converting Z' into Z. In the formula, the groups convertible to Z include cyano, halogen and other functional groups.

Suitable bases include alkali metal hydroxides such as sodium hydroxide or potassium hydroxide; alkali metal carbonates such as sodium carbonate, potassium carbonate, sodium bicarbonate; alcoholates such as sodium ethylate and tertiary amines such as triethylamine, dimethyl aniline or pyridine, etc.

Suitable reaction media include water, acetone, methylethyl ketone, methanol, isopropanol, butanol, dimethylformamide, dimethylsulfoxide, tetrahydrofuran, benzene, toluene, xylene, chlorobenzene, chloroform, carbon tetrachloride, dichloroethane, etc.

The resulting compound can be converted into a desired phenoxyphenoxy unsaturated derivative by the following processes.

The object compounds of phenoxyphenoxy unsaturated derivatives (I) can be produced directly reacting a phenoxyphenol having the formula

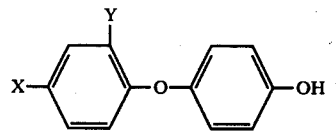

with a halopentenoic compound or a halopentenol compound having the formula

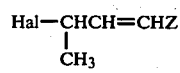

in the presence of a base in suitable solvent at 0° to 150° C. for 1 to 20 hours.

The object compounds of phenoxyphenoxy unsaturated acid esters having the formula

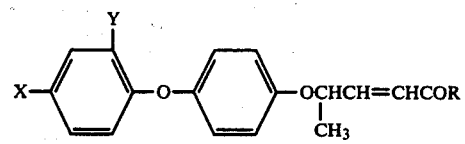

can be produced by reacting the phenoxyphenol having the formula

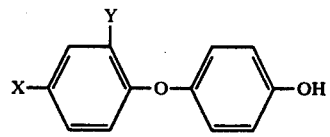

with a halopentenoic acid to produce a phenoxyphenoxy unsaturated acid having the formula

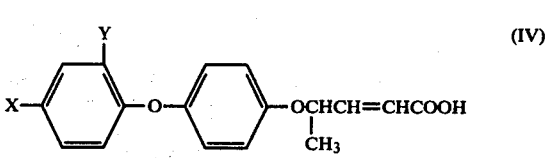    (IV)

and then, reacting the corresponding compound having the formula ROH with the phenoxyphenoxy unsaturated acid (IV) or its acid halide having the formula

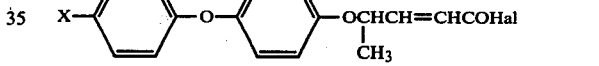    (IV')

in suitable solvent or without a solvent at 0° to 150° C. for 1 to 20 hours.

The phenoxyphenoxy unsaturated acid halide (IV') can be easily obtained by reacting a halogenating agent such as thionyl chloride, and phosphorus trihalides with the phenoxyphenoxy unsaturated acid (IV).

The object compounds of phenoxyphenoxy unsaturated acid amides having the formula

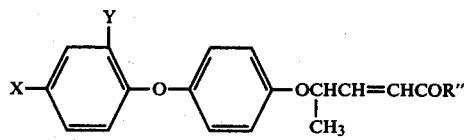

can be also produced by reacting the phenoxyphenoxy unsaturated acid (IV) or its acid halide (IV') with the corresponding amine or ammonia in suitable inert solvent with or without an alcoholate, sodium amide or sodium hydride, at 0° to 150° C. for 1 to 20 hours.

The object compounds of phenoxyphenoxy unsaturated acid thiol esters having the formula

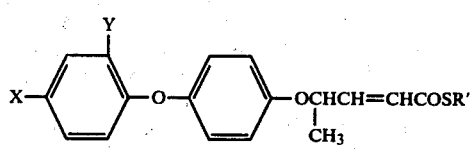

can be also produced by reacting the phenoxyphenoxy unsaturated acid (IV) or its acid halide (IV') with the corresponding mercaptan in the presence of a base as a dehydrohalogenation agent in suitable inert solvent or without a solvent at −10° to 150° C. for 1 to 20 hours.

The object compounds of phenoxyphenoxy pentenols having the formula

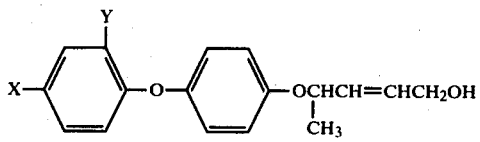

can be produced by hydrogenating the phenoxyphenoxy unsaturated acid (IV) or its acid halide (IV') or its ester, with a reducing agent such as sodium boron hydride and aluminum lithium hydride, in suitable insert solvent at −20° to 100° C. for 1 to 20 hours.

The object compounds of phenoxyphenoxy pentenol derivatives having the formula

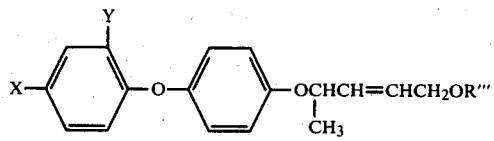

can be also produced by reacting the phenoxyphenoxy pentenol with a compound having the formula R'''OH or R'''NH₂ in suitable inert solvent at 0° to 150° C. for 1 to 20 hours.

These object compounds are produced by the main reaction of the phenoxyphenol (III) with the unsaturated halide (II) and if necessary, converting the product into the object compound.

The following shows certain processes for converting the product obtained by the main reaction.

(a) The phenoxyphenoxy unsaturated derivatives having the formula (I) can be produced by reacting a phenoxyphenoxy unsaturated acid having the formula

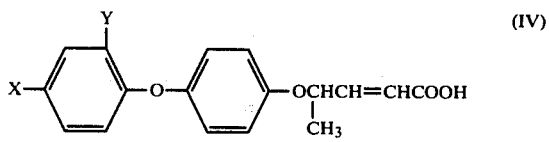

with a compound having the formula ROH (X, Y and R are defined above) in the presence of a catalyst such as an aromatic sulfonic acid such as benzenesulfonic acid, toluenesulfonic acid or β-naphthalenesulfonic acid; an anhydrous sulfate such as anhydrous copper sulfate or anhydrous iron sulfate; phosphorus oxychloride, phosphoric acid anhydride, boron trifluoride or acidic ion-exchanger at 20° to 150° C. or under refluxing for 1 to 20 hours.

(b) The phenoxyphenoxy unsaturated derivatives having the formula (I) can be produced by reacting a phenoxyphenoxy unsaturated acid having the formula

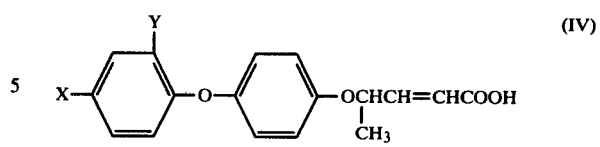

with a base such as alkali metal hydroxides, alkaline earth metal hydroxides and organic bases e.g. amines and amino compounds, in a reaction medium at 0° to 100° C. for 0.5 to 10 hours.

(c) The phenoxyphenoxy unsaturated derivatives having the formula (I) can be produced by reacting phenoxyphenoxy pentenoyl halide having the formula

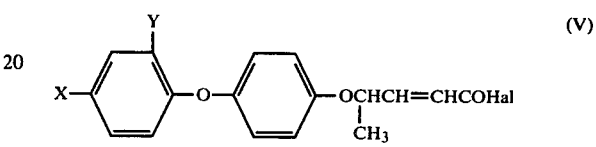

with a compound having the formula ROH, R'SH or R''H. (X, Y, R and Hal are defined above) in the absence of dehydrohalogenating agent of a base in a reaction medium or excess of the compound having the formula ROH or without a reaction medium, at −10° to 150° C. for 1 to 20 hours.

Suitable dehydrogenhalide agents of inorganic or organic bases include alkali metal hydroxides such as sodium hydroxide or potassium hydroxide; alkali metal carbonates such as sodium carbonate, potassium carbonate or sodium bicarbonates; alcoholates such as sodium ethylate; and tertiary amines such as triethyl amine, dimethyl aniline or pyridine.

Suitable reaction media include acetone, methyl ethyl ketone, dimethylformamide, dimethylsulfoxide, tetrahydrofuran, benzene, toluene, xylene, chlorobenzene, chloroform, carbon tetrachloride and dichloroethane.

The phenoxyphenoxy pentenoic halide (V) can be produced by reacting the phenoxyphenoxy unsaturated acid (IV) with thionyl chloride or phosphorus trihalide in a solvent.

(d) The phenoxyphenoxy pentenoate having the formula

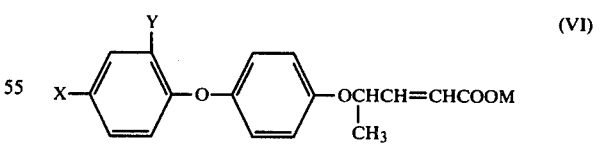

wherein M is an alkali metal, an alkaline earth metal, a heavy metal or an amino group including an alkylamino and an arylamino group; can be easily produced by neutralizing the corresponding acid or acid halide with the corresponding base.

The reaction is preferably carried out in a solvent at higher than room temperature.

(e) The phenoxyphenoxy pentenol derivatives having the formula

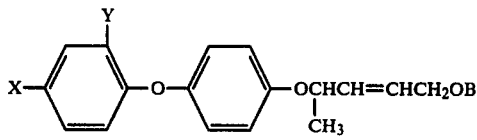

wherein R represents hydrogen atom, an alkyl carbonyl, haloalkyl carbonyl, an aryl carbonyl, an alkylamino carbonyl or an arylaminocarbonyl group can be easily produced by reacting 4-halogeno-2-pentenol or its ester with a phenoxyphenol having the formula

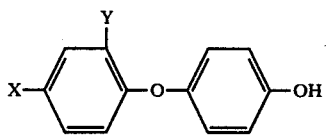

The reaction is preferably carried out in a solvent in the presence of a base.

When the phenoxyphenoxy pentenol (B=H) is produced, the product can be esterified to obtain the corresponding ester.

(f) The phenoxyphenoxy pentenols having the formula

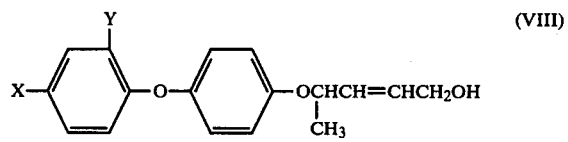

can be produced by reducing a phenoxyphenoxy unsaturated derivative having the formula

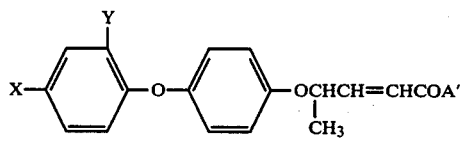

(A' is OR, or a halogen atom obtained in the processes of (a) (b) (c) (d) or (e) in the presence of a reducing agent such as lithium aluminum hydride and sodium boro hydride in a reaction medium at $-20°$ to $100°$ C. for 1 to 20 hours.

If necessary, the resulting phenoxyphenoxy pentenol is esterifying with the corresponding acid to obtain its esters.

Certain examples for producing the compounds by this process will be described.

PREPARATION 1—1

Ethyl 4-[4(2,4-dichlorophenoxy) phenoxy](2)-pentenoate

In 100 ml of dimethylformamide, 25.5 g (0.1 mole) of 4-(2,4-dichlorophenoxy) phenol was dissolved and 19.3 g (0.14 mole) of sodium carbonate and 24.8 g (0.12 mole) of ethyl 4-bromo-2-pentenoate were added. The mixture was stirred at 100° C. for 6 hours to react them. The reaction mixture was poured into water and the reaction product was extracted with dichloromethane. The dichloromethane phase was washed with water, with a dilute hydrochloric acid and then, with water and dehydrated over anhydrous sodium sulfate and dichloromethane was distilled off and the residue was distilled in vacuum to obtain 32.5 g (yield of 85.2%) of pale yellow viscous liquid having a boiling point of 180° to 190° C./0.007 mmHg and $N_D^{20}$ of 1.5566.

PREPARATION 1—2

Methyl 4-[4-(4-bromophenoxy) phenoxy](2)-pentenoate

A mixture of 73 g (0.2 mole) of 4[4-(4-bromophenoxy) phenoxy](2)-pentenoic acid, 200 ml of methanol and 10 g of conc. sulfuric acid was refluxed for 4 hours and about a half of methanol was distilled off and then, 300 ml of water was added to dilute it and the resulting oily product was extracted with ester and the ether phase was dehydrated over anhydrous sodium sulfate and ether was distilled off to obtain 66 g (yield of 87.5%) a brown transparent viscous liquid and $N_D^{20}$:1.5822.

PREPARATION 1-3

Isopropyl 4-[4-(4-iodophenoxy) phenoxy](2)-pentenoate

In 70 ml of isopropyl alcohol, 22 g (0.05 mole) of ethyl 4-[4-(4-iodophenoxy) phenoxy]2-pentenoate and 3 g of sulfuric acid were added and the mixture was refluxed for 15 hours to react them, and about 50 ml of isopropyl alcohol was distilled off and 150 ml of water was added and the resulting oily product was extracted with ether. The ether phase was washed with water and dehydrated over anhydrous sodium sulfate and ether was distilled off to obtain a dark brown viscous liquid having $N_D^{20}$:1.5753 (yield of 74.0%).

PREPARATION 1-4

N-sec butyl 4-[4-(4-bromophenoxy) phenoxy](2)-pentenamide

In 100 ml of methanol, 18.9 g of methyl 4-[4-(4-bromophenoxy) phenoxy]2-pentenoate was dissolved and 20 ml of 4% an aqueous solution of sec-butylamine was added to react them at room temperature for 4 hours. After the reaction, water was added to precipitate crystals and then, the product was recrystallized from methanol/water to obtain 15.8 g (yield 75.5%) of brown color crystals having a melting point of 127° to 128° C.

PREPARATION 1-5

4-[4-(4-chlorophenoxy) phenoxy](2)-pentenamide

A mixture of 6.4 g (0.02 mole) of 4-[4-(4-chlorophenoxy) phenoxy]2-pentenoic acid and 30 ml of thionyl chloride was refluxed for 6 hours.

Excess of thionyl chloride was removed from the reaction mixture and the residue of the acyl chloride was dissolved in 20 ml of acetone and 50 ml of 5% ammonia water was added to react them at room temperature for 1 hour and crystals were separated and washed with water and recrystallized from water-ethanol to obtain 5.2 g (yield 81.8%) of pale yellow powdery crystals having a melting point of 135° to 137° C.

In accordance with the same process, Compounds No. 1-6, 12, 19, 20, 21 and 27 were produced by using the corresponding amine and the corresponding pentenoic acid.

PREPARATION 1-6

Methyl 4-[4-(4-bromophenoxy) phenoxy](2)-pentenoate

In 250 ml of anhydrous methanol, 37.0 g (0.1 mole) of 4-[4-(4-bromophenoxy) phenoxy](2)-pentenoyl chloride was added under cooling and the mixture was stirred at room temperature for 2 hours and at 40° to 45° C. for 2 hours and excess of methyl alcohol was distilled off to obtain 35.2 g (yield 93.0%) of brown transparent viscous liquid having $N_D^{20}$:1.5822.

In accordance with the same process, Compounds No. 1-3, 4, 5, 8, 9, 10, 11, 14, 15, 16, 17, 22, 25 and 26 were produced by using the corresponding alcohol and the corresponding acyl chloride.

PREPARATION 2-1

Ethyl 4-[4-(4-bromo-2-chlorophenoxy)phenoxy](2)-pentenoate

In 60 ml of ethanol, 9.0 g (0.03 mole) of 4-(4-bromo-2-chlorophenoxy) phenol and 7.6 g (0.036 mole) of ethyl 4-bromo-2-penetenoate were dissolved and 4.6 g (0.033 mole) of potassium carbonate was added and the mixture was refluxed for 3 hours to react them. The reaction product was extracted with ether and the ether phase was washed with water and dehydrated over anhydrous sodium sulfate and ether was distilled off and lower boiling materials having boiling point of lower than 140° C./0.01 mmHg were distilled off to obtain 11.7 g of an orange viscous liquid having $N_D^{20}$:1.5794. (yield: 91.5%).

PREPARATION 2—2

Isopropyl 4-[4-(2-chloro-4-bromo-phenoxy) phenoxy]-2-pentenoate

A mixture of 19.9 g (0.05 mole) of 4-[4-(2-chloro-4-bromophenoxy) phenoxy[(2)-pentenoic acid, 50 ml of isopropanol, 50 ml of benzene and 3 g of conc. sulfuric acid was refluxed under removing water by a trap for 5 hours. After the reaction, 100 ml of water was added and the benzene phase was washed sequentially with 5% aqueous solution of sodium hydroxide, water, a dilute hydrochloric acid and water, and dehydrated over anhydrous sodium sulfate and benzene was distilled off to obtain 17.9 g of an orange viscous liquid having $N_D^{20}$:1.5710. (yield: 81.5%).

PREPARATION 2-3

2-Chloroethyl 4-[4-(2-chloro-4-bromophenoxy) phenoxy](2)-pentenoate

A mixture of 11.9 g (0.03 mole) of 4-[4-(2-chloro-4-bromophenoxy) phenoxy]2-pentenoic acid and 20 ml of thionyl chloride was refluxed for 6 hours. Excess of thionyl chloride was distilled off from the reaction mixture and 20 ml of 2-chloroethanol was added to the residue of the acyl chloride, and the mixture was gradually heated to react them at 60° C. for 5 hours and excess of 2-chloroethanol was distilled off to obtain 11.4 g of an orange viscous liquid having $N_D^{20}$:1.5902. (yield: 89.0%).

PREPARATION 2-4

Allyl 4-[4-(2-chloro-4-bromophenoxy) phenoxy]2-pentenoate

In a mixture of 70 ml of benzene, 2.1 g (0.030 mole) of allyl alcohol and 2.6 g (0.033 mole) of pyridine, 12.5 g (0.03 mole) of [4-(2-chloro-4-bromophenoxy) phenoxy]2-pentenoic chloride obtained in the previous Preparation was added to react them at room temperature. Water was added to the reaction mixture and the benzene phase was washed with water and dehydrated over anhydrous sodium sulfate and benzene was distilled off to obtain 11.5 g of an orange viscous liquid having $N_D^{20}$:1.5757 (yield 87.3%).

In accordance with the same process, Compounds No. 2-1, 2, 3, 5 and 6 were produced by using the corresponding alcohol.

PREPARATION 3-1

4-[4-(4-clorophenoxy) phenoxy]2-pentenoic acid dimethylamine salt

In 15 ml of 10% dimethylamine aqueous solution, 7.0 g (0.02 mole) of 4-[4-(4-chlorophenoxy) phenoxy]2-pentenoic acid was dissolved and then, excess of dimethylamine and water was removed by a rotary evaporator to obtain 6.5 g of an orange viscous liquid, (yield: 92.2%).

In accordance with the same process, Compound No. 3-5 was produced by using the corresponding amine.

PREPARATION 4-1

Methoxyethyl 4-[4-(4-trifluoromethylphenoxy) phenoxy](2)-pentenoate

In 70 ml of ethanol, 10.2 g (0.04 mole) of 4-(trifluoromethylphenoxy) phenol and 11.4 g (0.048 mole) of methoxyethyl 4-bromo-2-pentenoate were dissolved and 6.1 g (0.044 mole) of potassium carbonate was added and the mixture was refluxed for 4 hours to react them. The reaction mixture was extracted with ether and the ether phase was washed with water and dehydrated over anhydrous sodium sulfate, and then, ether was distilled off and lower boiling materials having boiling point of lower than 140° C./0.01 mmHg was distilled off to obtain 15.2 g of an orange viscous liquid having $N_D^{20}$:1.5156 (yield: 92.3%).

PREPARATION 4-2

Ethoxyethyl 4-[4-(4-trifluoromethylphenoxy) phenoxy](2)-pentenoate

A mixture of 17.7 g (0.05 mole) of 4-[4-( 4-trifluoromethylphenoxy) phenoxy]2-pentenoic acid, 50 ml of ethyl cellosolve, 50 ml of benzene and 3 g of conc. sulfuric acid was refluxed under removing water by a trap for 4 hours. After the reaction, 100 ml of benzene was added to dilute the product and the benzene phase was washed with water and dehydrated over anhydrous sodium sulfate and then benzene was distilled off and lower boiling materials having boiling point of lower than 140° C./0.01 mmHg were distilled off to obtain 17.9 g of an orange viscous liquid having $N_D^{20}$:1.5134 (yield: 84.4%).

PREPARATION 4-3

1-Methoxypropyl 4-[4-(4-bromo-2-clorophenoxy) phenoxy](2)-pentenoate

A mixture of 14.2 g of 4-[4-(4-bromo-2-chlorophenoxy) phenoxy]2-pentenoic acid and 25 ml of thionyl chloride was refluxed for 6 hours to react them. Excess of thionyl chloride was distilled off from the reaction mixture and 15 ml of 2-methoxypropyl alcohol was added to the residue of the acid chloride. After the addition, the mixture was gradually heated to react them at 60° C. for 5 hours and excess of 2-methoxypropyl alcohol was distilled off under a reduced pressure to obtain 17.2 g of an orange viscous liquid having $N_D^{20}$:1.5210 (yield: 91.3%).

PREPARATION 4—4 n-Butoxyethyl 4-[4-(4-bromo-2-chlorophenoxy) phenoxy](2)-pentenoate

In a mixture of 70 ml of toluene, 4.7 g (0.04 mole) of n-butoxyethanol and 4.6 g (0.033 mole) of potassium carbonate, 12.5 g (0.03 mole) of 4-[4-(4-bromo-2-chlorophenoxy) phenoxy] 2-pentenoyl chloride obtained in the previous Preparation, was added and the mixture was gradually heated at 50° to 60° C. for 1 hour. The toluene phase was sequentially washed with water, 5% aqueous solution of sodium hydroxide and water and dehydrated over anhydrous sodium sulfate and then, toluene was distilled off to obtain 13.7 g of an orange viscous liquid having $N_D^{20}$:1.5108 (yield: 92.0%).

In accordance with the same process, Compounds No. 4–1, 2, 3, 4, 5, 6 and 8 were produced by using the corresponding alcohol.

Preparation 4–5

Methoxymethyl 4-[4-(4-trifluoromethylphenoxy) phenoxy](2)- pentenoate

In 100 ml of acetone, 11.2 g (0.03 mole) of sodium 4-[4-(4-trifluoromethylphenoxy) phenoxy](2)-pentenoate was suspended, and then, 3.6 g (0.045 mole) of methoxymethyl chloride was added and the mixture was stirred at room temperature for 3 hours and then, refluxed for 8 hours to react them. After the reaction, the reaction product was extracted with ether and the ether phase was sequentially washed with water. 5% aqueous solution of sodium hydroxide and water and dehydrated over anhydrous sodium sulfate, and then, ether was distilled off and lower boiling materials having boiling point of lower than 140° C./0.01 mmHg were distilled off in vacuum to obtain 8.7 g of an orange viscous liquid having $N_D^{20}$:1.5208 (yield: 77.6%).

PREPARATION 5–1

N,N-diethyl 4-[4-(4-trifluoromethylphenoxy) phenoxy](2)-pentenamide

In 300 ml of acetone, 25.4 g (0.1 mole) of 4-(4-trifluoromethylphenoxy) phenol was dissolved and 19.3 g of sodium carbonate was added and 23.4 g (0.1 mole) of N,N-diethyl 4-bromo (2)-potenamide was added under stirring and the mixture was stirred at 60° C. for 2 hours. The reaction mixture was poured into ice water and an oily product was extracted with ether and the ether phase was washed with water and dehydrated and ether was distilled off and the residue was distilled off in vacuum to obtain 36.2 g of an orange viscous liquid having a boiling point of 190° to 190° to 192° C./0.015 mmHg and $N_D^{20}$:1.5323 (yield: 89.2%).

PREPARATION 5–2

4-[4-(4-trifluoromethylphenoxy) phenoxy](2)-pentenamide

A mixture of 7.4 g (0.02 mole) of 4-[4-(4-trifluoromethylphenoxy) phenoxy](2)-pentenoic acid and 30 ml of thionyl chloride was refluxed for 6 hours to react them. Excess of thionyl chloride was distilled off from the reaction mixture and the residue of the acyl halide was dissolved in 20 ml of acetone and 50 ml of 5% ammonia water was added to react them at room temperature for 1 hour.

The resulting precipitate was filtered and recrystallized from water-ethanol to obtain 5.7 g of white crystals having m.p. of 140° to 142° C. (yield: 81.4%).

In accordance with the same process, Compounds No. 5—5 to 5-10 were produced by using the corresponding amine.

PREPARATION 6-1

Phenyl 4-[4-(4-trifluoromethylphenoxy) phenoxy](2)-pentenoate

In 50 ml of ethanol, 12.7 g (0.05 mole) of 4-(4-trifluoromethylphenoxy) phenol, 12.8 g (0.05 mole) of phenyl 4-bromo (2)-pentenoate and 7 g (0.05 mole) of anhydrous potassium carbonate were added and the mixture was refluxed under stirring for 3 hours. After the reaction, the reaction mixture was poured into 200 ml of ice water and an oily product was extracted with toluene and the toluene phase was sequentially washed with 5% aqueous solution of sodium hydroxide, and water and dehydrated over anhydrous magnesium sulfate and toluene was distilled off under a reduced pressure and the residue was heated at 110° C. under a reduced pressure 0.05 mmHg to obtain 19.5 g of a yellow viscous liquid having $N_D^{20}$:1.5471 (yield: 91.1%).

PREPARATION 6-2

Dimethylaminoethyl 4-[4-(4-trifluoromethylphenoxy) phenoxy](2)-pentenoate

In 50 of benzene, 7.4 g (0.02 mole) of 4-[4-(4-trifluoromethylphenoxy) phenoxy](2)-pentenoyl chloride and 3.6 g (0.04 mole) of dimethylaminoethanol were added and the mixture was heated at 50° C. for 3 hours to react them. After the reaction, the benzene solution was sequentially washed with water, 5% aqueous solution of sodium carbonate and water and dehydrated over anhydrous sodium sulfate and benzene was distilled off and low boiling materials were distilled off at 115° C. under 0.095 mmHg to obtain 8.0 g of pale yellowish orange viscous liquid having $N_D^{20}$:1.5178 (yield 94.1%).

PREPARATION 6-3

3-Methoxy-3-methylbutyl 4[4-(4-trifluoromethylphenoxy) phenoxy](2)-pentenoate

In 40 ml of benzene, 5.0 g (0.013 mole) of 4-[4-(4-trifluoromethylphenoxy) phenoxy] (2)-pentenoyl chloride and 2.1 g (0.018 mole) of 3-methoxy-3-methylbutanol were dissolved and the mixture was refluxed for 6 hours under stirring. The reaction was performed under generating hydrogen chloride gas. The reaction mixture was cooled and mixed with 100 ml of benzene and the benzene phase was washed two times with 50 ml of saturated aqueous solution of sodium bicarbonate and two times with water and dehydrated over anhydrous sodium sulfate and benzene was distilled off and lower boiling materials were distilled off at 110° C. under 0.08 mmHg to obtain 5.9 g of pale brown viscous liquid having $N_D^{20}$:1.5099 (yield: 98.3%).

In accordance with the same process, Compounds No. 6–1 to 6–17 were also produced by using the corresponding alcohol.

PREPARATION 7-1

S-ethyl 4-[4-(4-trifluoromethylphenoxy)phenoxy](2)-pententhiolate

In 70 ml of ethanol, 11.1 g (0.05 mole) of ethyl 4-bromo-(2)-pententhiolate and 10.2 g (0.04 mole) of 4-(4-trifluoromethylphenoxy) phenol were dissolved and 6.1 g (0.044 mole) of potassium carbonate was added and the mixture was refluxed for 4 hours. The reaction mixture was extracted with ether and the ether phase was washed with water and dehydrated over anhydrous sodium sulfate and ether was distilled off and lower boiling materials were distilled off at 140° C. under 0.01 mmHg to obtain 14.7 g of an orange transparent liquid having $N_D^{20}$:1.5455 (yield:91.7%).

PREPARATION 7-2

S-methyl 4-[4-(4-trifluoromethylphenoxy)phenoxy](2)-pententhiolate

In 100 ml of toluene, 2.9 g (0.06 mole) of methylmercaptance and 7.6 g (0.055 mole) of potassium carbonate were dissolved and 20.5 g (0.05 mole) of 4-[4-(4-trifluoromethylphenoxy)phenoxy](2)-pentenoyl bromide was added at 5° to 10° C. to react them at room temperature for 4 hours. Water was added to the reaction mixture and the toluene phase was washed with water and dehydrated over anhydrous sodium sulfate and toluene was distilled off to obtain 16.7 g of an orange viscous liquid having $N_D^{20}$:1.5502 (yield:86.9%).

In accordance with the same process, Compounds No. 7-2 to 7-9 were produced by using the corresponding mercaptane.

PREPARATION 8-1

4-[4-(4-trifluoromethylphenoxy)phenoxy](2)-pentene-1-ol

In 50 ml of dehydrated diethyl ether, 0.9 g (0.02 mole) of lithium aluminum hydride was suspended and then a solution of 11.1 g (0.03 mole) of 4-[4-(4-trifluoromethylphenoxy)phenoxy](2)-pentenoyl chloride in 50 ml of diethyl ether was added at 5° to 10° C. under cooling with ice water. After the addition, the mixture was reacted at room temperature for 2 hours and excess lithium aluminum hydride was decomposed by adding ethyl acetate containing water and the mixture was filtered and the filtrate of the ether phase was washed with water and dehydrated over anhydrous sodium sulfate and ether was distilled off to obtain 8.4 g of a pale orange viscous liquid having $N_D^{20}$:1.5330 (yield:82.5%).

PREPARATION 8-2

4-[4-(4-bromophenoxy)phenoxy](2)-penten-1-ol

In 50 ml of dioxane, 0.8 g (0.02 mole) of sodium boron hydride was suspended and a solution of 7.6 g (0.02 mole) of 4-[4-(4-bromophenoxy)phenoxy](2)-pentenoyl chloride in 30 ml of dioxane was added. The mixture was reacted at room temperature for 1 hour and at 45° to 50° C. for 1 hour. Acetic acid was added to the reaction mixture to decompose excess of sodium boro hydride and the product was extracted with ether and the ether phase was washed with water and dehydrated over anhydrous sodium sulfate and ether was distilled off to obtain 5.5 g of a pale orange viscous liquid having $N_D^{20}$:1.5978 (yield:79.0%).

In accordance with the same process, Compounds No. 8-3, 4, 5 and 6 were produced by using the corresponding starting material.

PREPARATION 9-1

4-[4-(4-trifluoromethylphenoxy)phenoxy](2)-pentenyl acetate

In 50 ml of acetone, 6.8 g (0.02 mole) of 4-[4-(4-trifluoromethylphenoxy)phenoxy](2)-pentenol was dissolved and 3.0 g (0.022 mole) of potassium carbonate and 1.7 g (0.022 mole) of acetylchloride were added and the mixture was refluxed for 2 hours to react them. The reaction mixture was cooled and poured into water and the product was extracted with benzene and sequentially washed with 5% aqueous solution of sodium hydroxide and water and dehydrated over anhydrous sodium sulfate and benzene was distilled off and lower boiling materials were distilled off at 120° C. under 0.1 mmHg to obtain 6.7 g of a brown viscous liquid having $N_D^{20}$:1.5359 (yield:88.2%).

In accordance with the same process, Compounds No. 9-2, 3, and 4 were produced by using the corresponding starting compound.

PREPARATION 9-2

N-methyl 4-[4-(4-trifluoromethylphenoxy)phenoxy](2)-pentenyl carbamate

In 50 ml of benzene, 6.8 g (0.02 mole) of 4-[4-(4-trifluoromethylphenoxy)phenoxy](2)-pentenol and 1.4 g (0.025 mole) of methyl isocyanate were dissolved and the mixture was stirred for 1 hour at room temperature and then refluxed for 1 hour and the reaction product was washed with water and the benzene phase was dehydrated over anhydrous sodium sulfate and benzene was distilled off and lower boiling materials were distilled off at 120° C. under 0.1 mmHg to obtain 7.3 g of a brown viscous liquid having $N_D^{20}$:1.5447 (yield:92.4%).

In accordance with the same process, Compound No. 9-6 was produced by using phenylisocyanate.

The typical compounds obtained by said processes will be exemplified. The compound numerals are referred in the following description.

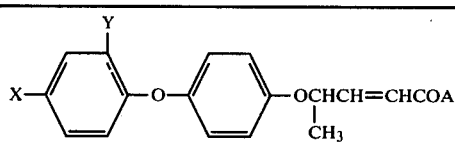

| Compound No. | X | Y | A | Property mp (°C.) bp (mm Hg) | $N_D^{20}$ |
|---|---|---|---|---|---|
| 1-1 | I | H | OH | mp 152–155° C. | |
| 1-2 | I | H | OCH$_3$ | | 1.5619 |
| 1-3 | I | H | OC$_2$H$_5$ | | 1.5877 |
| 1-4 | I | H | OC$_3$H$_7$—i | | 1.5753 |
| 1-5 | I | H | OC$_4$H$_9$—sec. | | 1.5667 |
| 1-6 | I | H | NHC$_4$H$_9$—sec. | mp 165.5–167.5° C. | |
| 1-7 | Br | H | OH | mp 140–142° C. | |
| 1-8 | Br | H | OCH$_3$ | | 1.5822 |
| 1-9 | Br | H | OC$_2$H$_5$ | | 1.5708 |
| 1-10 | Br | H | OC$_3$H$_7$—i | | 1.5724 |
| 1-11 | Br | H | OC$_4$H$_9$—sec. | | 1.5643 |

-continued

| | | | | | |
|---|---|---|---|---|---|
| 1-12 | Br | H | NHC4H9—sec. | mp 127–128° C. | |
| 1-13 | Cl | H | OH | mp 117° C. | |
| 1-14 | Cl | H | OCH3 | | 1.5745 |
| 1-15 | Cl | H | OC2H5 | | 1.5514 |
| 1-16 | Cl | H | OC4H9 | | 1.5547 |
| 1-17 | Cl | H | OCH2CH=CH2 | | 1.5600 |
| 1-18 | Cl | H | NH2 | mp 135–137° C. | |
| 1-19 | Cl | H | N(CH3)2 | | 1.5710 |
| 1-20 | Cl | H | NH—C6H5 | mp 177° C. | |
| 1-21 | Cl | H | NH—C6H4—Cl | mp 150° C. | |
| 1-22 | F | H | OC2H5 | | 1.6663 |
| 1-23 | Cl | Cl | OH | mp 79–81° C. | |
| 1-24 | Cl | Cl | OCH3 | | 1.5778 |
| 1-25 | Cl | Cl | OC2H5 | bp 180–190° C. (0.007mm) | 1.5566 |
| 1-26 | Cl | Cl | OC3H7—i | | 1.565 |
| 1-27 | Cl | Cl | NH2 | mp 105–107° C. | |
| 2-1 | Br | Cl | OCH3 | | 1.5695 |
| 2-2 | Br | Cl | OC2H5 | | 1.5794 |
| 2-3 | Br | Cl | OC3H7—i | | 1.5710 |
| 2-4 | Br | Cl | OCH2CH=CH2 | | 1.5735 |
| 2-5 | Br | Cl | OCH2C≡CH | | 1.5930 |
| 2-6 | Br | Cl | OCH2CH2Cl | | 1.5902 |
| 3-1 | Cl | Cl | ONa | mp 232–237° C. | |
| 3-2 | Cl | Cl | OFe ½ | mp 108° C. | |
| 3-3 | Cl | H | OK | mp 244–247° C. | |
| 3-4 | Cl | H | ONH2(CH3)2 | — | |
| 3-5 | Cl | H | ONH2(C2H5)2 | — | |
| 3-6 | Br | H | OZn ½ | mp 185–188° C. | |
| 4-1 | CF3 | H | OCH2OCH3 | | 1.5208 |
| 4-2 | CF3 | H | OCH2CH2OCH3 | | 1.5156 |
| 4-3 | Cl | H | OCH2CH2OCH3 | | 1.5495 |
| 4-4 | Br | H | OCH2CH2OCH3 | | 1.5667 |
| 4-5 | CF3 | H | OCH2CH2OC2H5 | | 1.5134 |
| 4-6 | Br | Cl | OCH2CH2OC4H9(n) | | 1.5108 |
| 4-7 | Br | Cl | OCH2CHOCH3 \| CH3 | | 1.5210 |
| 4-8 | Br | Cl | OCH2CH2CHOCH3 \| CH3 | | 1.5110 |
| 5-1 | CF3 | H | OH | mp 129–132° C. | |
| 5-2 | CF3 | H | ONa | decomp 244° C. | |
| 5-3 | CF3 | H | OH.NH(CH3)2 | soluble as aq.sol. | |
| 5-4 | CF3 | H | NH2 | mp 140–142° C. | |
| 5-5 | CF3 | H | NHCH3 | mp 105–107° C. | |
| 5-6 | CF3 | H | NHC3H7 | mp 111° C. | |
| 5-7 | CF3 | H | N(C2H5)2 | bp 190–192° C. (0.05mm) | |
| 5-8 | CF3 | H | NH—C6H5 | mp 144–146° C. | |
| 5-9 | CF3 | H | NH—C6H4—Cl | mp 149° C. | |
| 5-10 | CF3 | H | NH—C6H4—CH3 | mp 131° C. | |
| 5-11 | CF3 | Cl | OH | mp 88–89° C. | |
| 6-1 | CF3 | H | OCH2CH2CN | bp >115° C. (0.06mm) | 1.5274 |
| 6-2 | CF3 | H | OCH2CH2N(CH3)2 | >115° C. (0.095mm) | 1.5178 |
| 6-3 | CF3 | H | OCH2CH2N(C2H5)2 | >130° C. (0.15mm) | 1.5139 |
| 6-4 | CF3 | H | OC2H4.O.C2H4OCH3 | >110° C. (0.06mm) | 1.5168 |
| 6-5 | CF3 | H | OC2H4.O.C2H4OC2H5 | >105° C. (0.05mm) | 1.5148 |
| 6-6 | CF3 | H | O—C6H5 | >110° C. (0.05mm) | 1.5471 |
| 6-7 | CF3 | H | O—C6H4—Cl | >100° C. (0.04mm) | 1.5528 |
| 6-8 | CF3 | H | O—C6H3Cl2 | >120° C. (0.08mm) | 1.5439 |
| 6-9 | CF3 | H | OCH2—C6H5 | >125° C. (0.09mm) | 1.5459 |
| 6-10 | CF3 | H | OCH2—C6H4—Cl | >125° C. (0.05mm) | 1.5528 |
| 6-11 | CF3 | H | OCH2—C6H4—CH3 | >145° C. (0.3mm) | 1.5461 |
| 6-12 | CF3 | H | OCH2—C6H3(CH3)2 | >165° C. (0.28mm) | 1.5430 |
| 6-13 | CF3 | H | OCH2—(2-pyridyl) | >85° C. (0.05mm) | 1.5472 |
| 6-14 | CF3 | H | OCH2—(3-pyridyl) | >125° C. (0.05mm) | 1.5503 |
| 6-15 | CF3 | H | OCH2—(furyl) | >120° C. (0.1mm) | 1.5574 |
| 6-16 | CF3 | H | O—C5H9 | >105° C. (0.22mm) | 1.5240 |
| 6-17 | CF3 | H | O—C6H11 | >100° C. (0.12mm) | 1.5224 |
| 6-18 | CF3 | H | OC2H4.C(CH3)2COCH3 | bp >110° C. (0.08mm) | |

-continued

| Compound No. | X | Y | Z | Property mp (°C.) bp (mmHg) | $N_D^{20}$ |
|---|---|---|---|---|---|
| 6-19 | CF₃ | H | O—⟨C₆H₄⟩—CH₃ (with H₃C) | >120° C. (0.05mm) | 1.5216 |
| 7-1 | CF₃ | H | SCH₃ | | 1.5522 |
| 7-2 | CF₃ | H | SC₂H₅ | | 1.5455 |
| 7-3 | Br | H | SC₃H₇—i | | |
| 7-4 | CF₃ | H | SC₄H₉—n | | 1.5355 |
| 7-5 | CF₃ | H | S—⟨C₆H₅⟩ | bp >122° C. (0.03mm) | 1.5870 |
| 7-6 | CF₃ | H | S—⟨C₆H₄⟩—Cl | >125° C. (0.03mm) | 1.5962 |
| 7-7 | CF₃ | H | S—⟨C₆H₃Cl₂⟩ | >110° C. (0.37mm) | |
| 7-8 | CF₃ | H | SCH₂—⟨C₆H₄⟩—Cl | >110° C. (0.1mm) | 1.5818 |
| 7-9 | CF₃ | H | SCH₂—⟨C₆H₄⟩—OCH₃ | >115° C. (0.14mm) | 1.5731 |

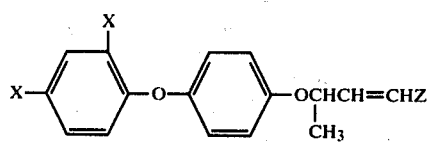

| Compound No. | X | Y | Z | Property mp (°C.) bp (mmHg) | $N_D^{20}$ |
|---|---|---|---|---|---|
| 8-1 | CF₃ | H | CH₂OH | | 1.5330 |
| 8-2 | Br | H | CH₂OH | | 1.5978 |
| 8-3 | Cl | H | CH₂OH | | |
| 8-4 | Cl | Cl | CH₂OH | | |
| 8-5 | Br | Cl | CH₂OH | | |
| 8-6 | CF₃ | Br | CH₂OH | | |
| 9-1 | CF₃ | H | CH₂OCOCH₃ | bp >120° C. (0.1mm) | 1.5359 |
| 9-2 | CF₃ | H | CH₂OCOCH₂Cl | >130° C. (0.1mm) | 1.5446 |
| 9-3 | CF₃ | H | CH₂OCO—⟨C₆H₅⟩ | >140° C. (0.1mm) | 1.5499 |
| 9-4 | CF₃ | H | CH₂OCOOC₂H₅ | >140° C. (0.1mm) | 1.5383 |
| 9-5 | CF₃ | H | CH₂OCONHCH₃ | >120° C. (0.1mm) | 1.5447 |
| 9-6 | CF₃ | H | CH₂OCONH—⟨C₆H₅⟩ | >140° C. (0.1mm) | 1.5548 |

The novel compounds of the present invention produced by said syntheses have significant herbicidal effect and non-phytotoxicity to many crop plants and can be applied to up-land, paddy fields, orchards, forests and non-cultured grounds by the soil treatment or the foliage treatment under selecting suitable method of application and suitable dose of the active ingredient.

The dose of the active ingredient of the compound of the present invention is depending upon a weather condition, a soil condition, a form of the composition, a season of the application and a method of the application and kinds of crop plants and kinds of weeds and it is usually in a range of 0.01 to 10 kg preferably 0.1 to 5 kg especially 0.5 to 3 kg per 1 hectare in the treatment and it is usually applied in a concentration of 10 to 10,000 ppm preferably 100 to 5,000 ppm especially 250 to 3,000 ppm of the active ingredient.

When the compound of the present invention is used as the herbicide, the compound can be used in the original form and also in the form of compositions such as granules, wettable powder, dusts, emulsifiable concentrates, fine power, floables, suspensions, etc to impart superior effect.

In the preparation of the herbicidal compositions, the compound of the present invention can be uniformly mixed with or dissolved in suitable adjuvants such as solid carrier such as talc, bentonite, clay, kaolin, diatomaceous earth, silica gel, vermiculite, lime, siliceous sand, ammonium sulfate or urea; liquid carriers such as alcohols, dioxane, acetone, cyclohexanone, methyl naphthalene or dimethylformamide; surfactants as emulsifiers dispersing agents or wetting agents such as alkyl sulfate, alkylsulfonate, polyoxyetheyleneglycol ethers, polyoxyethylenealkylaryl ethers such as polyoxyethylenenonylphenol ether or polyoxyethylenesorbitane monoalkylate; and carboxymethyl cellulose, gum arabic and other adjuvants.

The amounts of the active ingredients, adjuvants and additives in the herbicidal compositions of the present invention will be further illustrated.

Wettable powder:

Active ingredient: 5 to 95 wt. % preferably 20 to 50 wt. %

Surfactant: 1 to 20 wt. % preferably 5 to 10 wt. %

Solid carrier: 5 to 85 wt. % preferably 40 to 70 wt. %

The active ingredient is admixed with the solid carrier and the surfactant and the mixture is pulverized.

Emulsifiable concentrate:

Active ingredient: 5 to 95 wt. % preferably 20 to 70 wt. %

Surfactant: 1 to 40 wt. % preferably 5 to 20 wt. %

Liquid carrier: 5 to 90 wt. % preferably 30 to 60 wt. %

The active ingredient is dissolved in the liquid carrier and the surfactant is admixed.

Dust:

Active ingredient: 0.5 to 10 wt. % preferably 1 to 5 wt. %

Solid carrier: 99.5 to 90 wt. % preferably 99 to 95 wt. %

The active ingredient is mixed with fine solid carrier and the mixture is pulverized.

Granule:

Active ingredient: 0.5 to 40 wt. % preferably 2 to 10 wt. %

Solid carrier: 99.5 to 60 wt. % preferably 98 to 90 wt. %

The active ingredient is sprayed on the solid carrier or further coated with the solid carrier to form the granule.

The other herbicides can be incorporated in the herbicidal composition of the present invention.

Suitable additional herbicides include; carboxylic acid type compounds such as 2,3,6-trichlorobenzoic acid and salts thereof, 2,3,5,6-tetrachlorobenzoic acid and salts thereof, 2-methoxy-3,5,6-trichlorobenzoic acid and salts thereof, 2-methoxy-3,6-dichlorobenzoic acid and salts thereof, 2-methyl-3,6-dichlorobenzoic acid and salts thereof, 2,3-dichloro-6-methylbenzoic acid and salts thereof, 2,4-dichlorophenoxyacetic acid and salts and esters thereof, 2,4,5-trichlorophenoxyacetic acid and salts and esters thereof, 2-methyl-4-chlorophenoxyacetic acid and salts and esters thereof, α-(2,4,5-trichlorophenoxy) propionic acid and salts and esters thereof, 2-(2,4-dichlorophenoxy) butyric acid and salts and esters thereof, 4-(2-methyl-4-chlorophenoxy) butyric acid and salts and esters thereof, 2,3,6-trichlorophenylacetic acid and salts thereof, 3,6-endoxohexahydrophthalic acid, dimethyl 2,3,5,6-tetrachloroterephthalate, trichloroacetic acid and salts thereof, 2,2-dichloropropionic acid and salts thereof and 2,3-dichloroisobutyric acid and salts thereof; and carbamic acid type compounds such as ethyl N,N-di(n-propyl) thiolcarbamate, propyl N,N-di(n-propyl) thiolcarbamate, ethyl N-ethyl-N-(n-butyl) thiolcarbamate, propyl N-ethyl-N-(n-butyl) thiolcarbamate, 2-chloroallyl N,N-diethyl dithiocarbamate, N-methyl dithiocarbamate, S-ethyl hexahydro-1H-azepine-1-carbothioate, S-4-chlorobenzyl N,N-diethyl thiolcarbamate, S-benzyl N,N-di-sec-butyl thiolcarbamate, isopropyl N-phenyl carbamate, isopropyl N-(m-chlorophenyl) carbamate, 4-chloro-2-butyl N-(m-chlorophenyl) carbamate, methyl N-(3,4-dichlorophenyl) carbamate and methyl sulfanyl carbamate; phenol type compounds such as dinitro-O-(sec-butyl) phenol and salts thereof and pentachlorophenol and salts thereof; urea type compounds such as 3-(3,4-dichlorophenyl)-1,1-dimethyl urea, 3-phenyl-1,1-dimethyl urea, 3-(3,4-dichlorophenyl)-3-methoxy-1,1-dimethylurea, 3-(4-chlorophenyl)-3-methoxy-1,1-dimethylurea, 3-(3,4-dichlorophenyl)-1-n-butyl-1-methylurea, 3-(3,4-dichlorophenyl)-1-methoxy-1-methylurea, 3-(4-chlorophenyl)-1-methoxy-1-methylurea, 3-(3,4-dichlorophenyl)-1,1,3-trimethylurea, 3-(3,4-dichlorophenyl)-1,1-diethylurea, 1-(2-methylcyclohexyl)-3-phenylurea, 1-(5-t-butyl-1,3,4-triadiazol-2-yl)-1,3-dimethylurea, 3-(3-chloro-4-methylphenyl)-1,1-dimethylurea, 3-(3-chloro-4-methoxyphenyl)-1,1-dimethylurea and dichloralurea; triazine type compounds such as 2-chloro-4,6-bis(ethylamino)-s-triazine, 2-chloro-4-ethylamino-6-isopropyl-amino-s-triazine, 2-chloro-4,6-bis(methoxypropylamino)-s-triazine, 2-methoxy-4,6-bis(isopropylamino)-s-triazine, 2-methylmercapto-4,6-bis(isopropylamino)-s-triazine, 2-methylmercapto-4,6-bis(ethylamino)-s-triazine, 2-methylmercapto-4-ethylamino-6-isopropylamino-s-triazine, 2-chloro-4,6-bis(isopropylamino)-s-triazine, 2-methoxy-4,6-bis(ethylamino)-s-triazine, 2-methoxy-4-ethylamino-6-isopropylamino-s-triazine, 2-methylmercapto-4-(2-methoxyethylamino)-6-isopropylamino-s-triazine, 2-(4-chloro-6-ethylamino-s-triazine-2-yl) amino-2-methyl propionitrile, 4-amino-6-t-butyl-3-methylthio-1,2,4-triazine-5-(4H)-one, and 3-cyclohexyl-6-dimethylamino-1-methyl-s-triazine-2,4-(1H, 3H) dione; ether type compounds such as 2,4-dichloro-4′-nitrodiphenyl ether, 2,4,6-trichloro-4′-nitrodiphenyl ether, 2,4-dichloro-6-fluoro-4′-nitrodiphenyl ether, 3-methyl-4′-nitrodiphenyl ether, 3,5-dimethyl-4′-nitrodiphenyl ether, 2,4′-dinitro-4-trifluoromethyl diphenyl ether, 2,4-dichloro-3′-methoxy-4′-nitrodiphenyl ether, 2-chloro-4-trifluoromethyl-4′-nitrodiphenyl ether, 2-chloro-4-trifluoromethyl-3′-ethoxy-4′-nitrodiphenyl ether, 2-chloro-4-trifluoromethyl-3′-carbethoxy-4′-nitrodiphenyl ether and 2-chloro-4-trifluoromethyl-3′-(1-carbethoxy) ethoxy-4′-nitrodiphenyl ether; anilide type compounds such as N-(3,4-dichlorophenyl) propionamide, N-(3,4-dichlorophenyl) methacrylamide, N-(3-chloro-4-methylphenyl)-2-methylpentamide, N-(3,4-dichlorophenyl)-trimethyl acetamide, N-(3,4-dichlorophenyl)-α,α-dimethyl valeramide, N-isoprophyl-N-phenyl-chloroacetamide, N-n-butoxymethyl-N-(2,6-diethylphenyl) chloroacetamide and N-n-methoxymethyl-N-(2,6-diethylphenyl)chloroacetamide; uracil type compounds such as 5-bromo-3-sec-butyl-6-methyluracil, 5-bromo-3-cyclohexyl-1,6-dimethyluracil, 3-cyclohexyl-5,6-trimethyleneuracil, 5-bromo-3-isopropyl-6-methyluracil, and 3-tert.-butyl-5-chloro-6-methyluracil; nitrile type compounds such as 2,6-dichlorobenzonitrile, diphenylacetonitrile, 3,5-dibromo-4-hydroxybenzonitrile, and 3,5-diiodo-4-hydroxybenzonitrile; others such as 2-chloro-N,N-diallylacetamide, N-(1,1-dimethyl-2-propyl)-3,5-dichlorobenzamide, maleic acid hydrazide, 3-amino-1,2,4-triazole, mono-sodium methane arsonate, di-sodium methane arsonate, N,N-dimethyl-α,α-diphenyl acetamide, N,N-di(n-propyl)-2,6-dinitro-4-trifluoromethyl aniline, N,N-di(n-propyl)-2,6-dinitro-4-methyl aniline, N,N-di(n-propyl)-2,6-dinitro-4-methylsulfonyl aniline, O-(2,4-dichlorophenyl)-O-methylisopropyl phosphoramide thioate, 4-amino-3,5,6-trichloropiclinic acid, 2,3-dichloro-1,4-naphthoquinone, dimethoxycarbonyl disulfide, 3-isopropyl-1H-2,1,3-benzothiadiazine-4(3H)-one-2,2-dioxide, 6,7-dihydrodipyridol [1,2-a:2′:1′-c]pyrazinium salt, 1,1′-dimethyl-4,4′-bipyridinium salt, 3,4,5,6-tetrahydro-3,5-dimethyl-2-thio-2H-1,3,5-thiadiazine, 1,2-dimethyl-3,5-diphenylpyrazolinium methyl sulfate, N-sec-butyl-2,6-dinitro-3,4-xylidine, N-sec.-butyl-4-t-butyl-2,6-dinitroaniline, $N^3,N^3$-diethyl-2,4-dinitro-6-trifluoromethyl-1,3-phenylenediamine, 1,1,1-trifluoro-(4′-phenylsulfonyl)-methane sulfono-O-toluidine, 2-(1-naphthoxy)-N,N-diethyl propionamide, 2-t-butyl-4-(2,4-dichloro-5-isopropoxyphenyl)-1,3,4-oxadiazoline-5-one, 4-chloro-5-methylamino-2-(α,α,α-trifluoro-m-tolyl)-3(2H)-pyridazinone, N-cyclopropylmethyl-α,α,α-trifluoro-2,6-dinitro-N-propyl-p-toluidine and N-phosphonomethyl glycine, etc.

When the other herbicide described is mixed with the compound of the present invention, the ratio of the compounds and the dose of the compounds are selected depending upon the selectivities and herbicidal effects of the compounds to the crop plants and the control of noxious weeds treated with them.

Certain examples of the preparation of the herbicidal compositions will be illustrated, however, the kinds and the ratio of the adjuvants are not limited and can be varied from the conventional consideration of the herbicidal compositions.

| Composition No. 1: Wettable powder: | |
|---|---|
| Active ingredient | 30 wt. % |
| Sodium higher alcohol sulfate | 5 wt. % |
| Clay | 65 wt. % |

These components were uniformly mixed and pulverized to prepare a wettable powder.

| Composition No. 2: Emulsifiable concentrate: | |
|---|---|
| Active ingredient | 25 wt. % |
| Polyoxyethylenealkylaryl ether | 10 wt. % |
| Calcium dinaphthylmethanesulfonate | 5 wt. % |
| Xylene | 60 wt. % |

These components were uniformly mixed to prepare an emulsifiable concentrate.

| Composition No. 3: Granules: | |
|---|---|
| Active ingredient | 3 wt. % |
| Bentonite | 40 wt. % |
| Clay | 50 wt. % |
| Sodium lignin sulfonate | 7 wt. % |

These components were uniformly mixed and pulverized and then, kneaded with water and granulated and dried to prepare granulates.

| Composition No. 4: Dust: | |
|---|---|
| Active ingredient | 2 wt. % |
| Clay | 98 wt. % |

The components were mixed and pulverized to prepare a dust.

| Composition No. 5: Wettable powder: | |
|---|---|
| Active ingredient | 30 wt. % |
| Kaolin | 43 wt. % |
| White carbon | 20 wt. % |
| Polyvinyl alcohol | 5 wt. % |
| Polyoxyethylenenonylphenol | 2 wt. % |

These components were uniformly mixed and pulverized to prepare a wettable powder.

| Composition No. 6: Emulsifiable concentrate: | |
|---|---|
| Active ingredient | 50 wt. % |
| Polyoxyethylenenonylphenol | 5 wt. % |
| Alkylarylsulfonate | 5 wt. % |
| Xylene | 40 wt. % |

These components were uniformly mixed to prepare an emulsifiable concentrate.

| Composition No. 7: Granules: | |
|---|---|
| Active ingredient | 5 wt. % |
| Siliceous sand | 92 wt. % |
| White carbon | 3 wt. % |

These components were uniformly mixed and pulverized and then, kneaded with water and granulated and dried to prepare granulate.

| Composition No. 8: Dust: | |
|---|---|
| Active ingredient | 3 wt. % |
| White carbon | 2 wt. % |
| Kaolin | 95 wt. % |

These components were mixed and pulverized to prepare a dust.

The herbicidal activity of the compounds of the present invention will be further illustrated by certain experimental tests.

In the experiments, the following reference compounds were used as comparative tests.

Reference Compound (I):

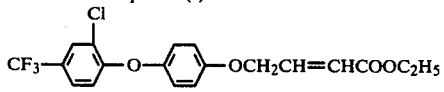

Reference Compound (II):

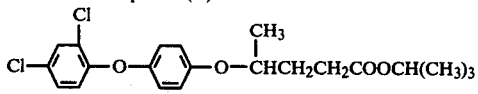

Reference Compound (III):

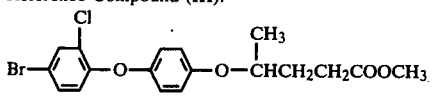

Reference Compound (IV):

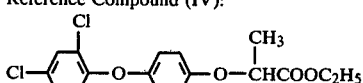

Reference Compound (V):

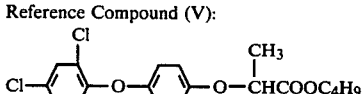

Reference Compound (VI):

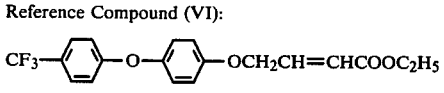

Reference Compound (VII):

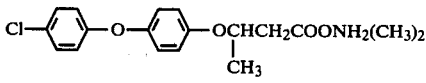

Reference Compound (VIII):

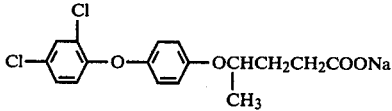

Reference Compound (IX):

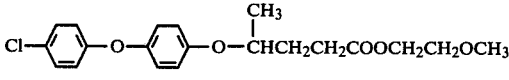

Reference Compound (X):

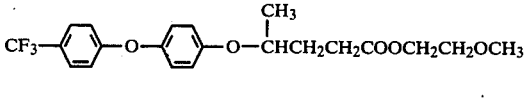

Reference Compound (XI):

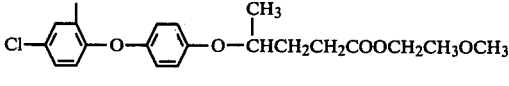

Reference Compound (XII):

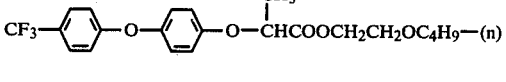

Reference Compound (XIII):

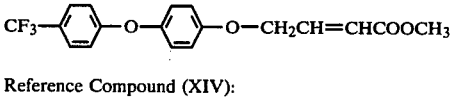

Reference Compound (XIV):

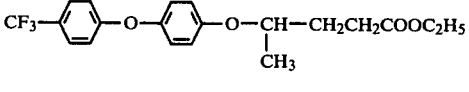

Reference Compound (XV):

-continued

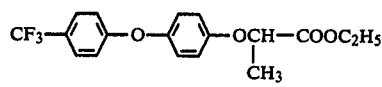

Reference Compound (XVI):

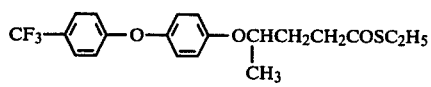

Reference Compound (XVII):

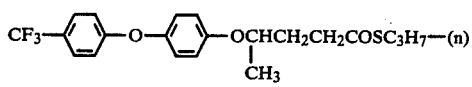

Reference Compound (XVIII):

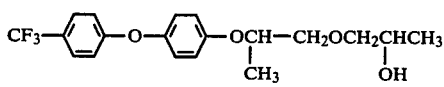

Reference Compound (XIX):

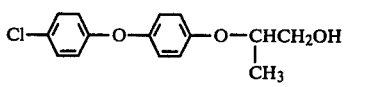

Reference Compound (XX):

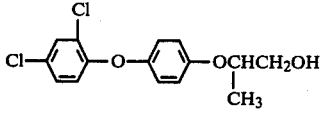

Reference Compound (XXI):

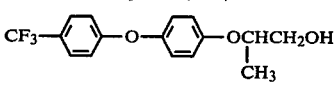

Reference Compound (XXII):

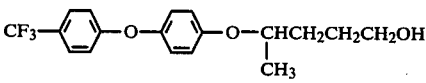

Reference Compound (XXIII):

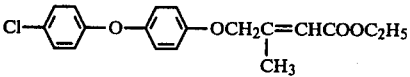

Reference Compound (XXIV):

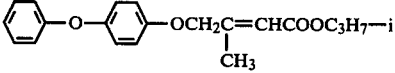

EXPERIMENT 1

Test for crop plants and up-land weeds in pre-emergence (pre-germination) soil treatment.

Each pot of 600 cm² was filled with up-land soil and seeds of wheat, barley, soybean, radish, barnyard grass and large crab grass were sown in a depth of 0.5 cm. Each emulsifiable concentrate prepared in accordance with the method of Composition No. 2 was diluted with water to give the specific concentration of the compound for the application of 1 Klit./ha. and the diluted solution was uniformly sprayed on the soil surface.

Twenty days after the treatment, the herbicidal effect and the phytotoxicity of the crop plants were observed and rated as follows:

The experiments were separately carried out as stated in Tables.

Herbicidal effect or phytotoxicity:

- 10: Complete growth suppression is found;
- 9: Growth suppression of from 90 to 100%;
- 8: Growth suppression of from 80 to 90%;
- 7: Growth suppression of from 70 to 80%;
- 6: Growth suppression of from 60 to 70%;
- 5: Growth suppression of from 50 to 60%;
- 4: Growth suppression of from 40 to 50%;
- 3: Growth suppression of from 30 to 40%;
- 2: Growth suppression of from 20 to 30%;
- 1: Growth suppression of from 0 to 20%;
- 0: No herbicidal effect.

TABLE 1

(Test 1-1)
Results of Tests in pre-emergence soil treatments

| Compound No. | Dose active ingredient (kg/ha) | Wh. | Ba. | So. | Ra. | B.G. | Cr.G. |
|---|---|---|---|---|---|---|---|
| Compound No. 1-1 | 0.5 | 0 | 0 | 0 | 0 | 10 | 10 |
|  | 0.25 | 0 | 0 | 0 | 0 | 10 | 10 |
| Compound No. 1-2 | 0.5 | 0 | 0 | 0 | 0 | 10 | 10 |
|  | 0.25 | 0 | 0 | 0 | 0 | 10 | 10 |
| Compound No. 1-3 | 0.5 | 0 | 0 | 0 | 0 | 10 | 10 |
|  | 0.25 | 0 | 0 | 0 | 0 | 10 | 10 |
| Compound No. 1-4 | 0,5 | 0 | 0 | 0 | 0 | 10 | 10 |
|  | 0.25 | 0 | 0 | 0 | 0 | 10 | 10 |
| Compound No. 1-5 | 0.5 | 0 | 0 | 0 | 0 | 10 | 10 |
|  | 0.25 | 0 | 0 | 0 | 0 | 10 | 10 |
| Compound No. 1-6 | 0.5 | 0 | 0 | 0 | 0 | 8 | 10 |
|  | 0.25 | 0 | 0 | 0 | 0 | 4 | 7 |
| Compound No. 1-7 | 0.5 | 0 | 0 | 0 | 0 | 10 | 10 |
|  | 0.25 | 0 | 0 | 0 | 0 | 10 | 10 |
| Compound No. 1-8 | 0.5 | 0 | 0 | 0 | 0 | 10 | 10 |
|  | 0.25 | 0 | 0 | 0 | 0 | 10 | 10 |
| Compound No. 1-9 | 0.5 | 0 | 0 | 0 | 0 | 10 | 10 |
|  | 0.25 | 0 | 0 | 0 | 0 | 10 | 10 |
| Compound No. 1-10 | 0.5 | 0 | 0 | 0 | 0 | 10 | 10 |
|  | 0.25 | 0 | 0 | 0 | 0 | 10 | 10 |
| Compound No. 1-11 | 0.5 | 0 | 0 | 0 | 0 | 10 | 10 |
|  | 0.25 | 0 | 0 | 0 | 0 | 10 | 10 |
| Compound No. 1-12 | 0.5 | 0 | 0 | 0 | 0 | 10 | 10 |
|  | 0.25 | 0 | 0 | 0 | 0 | 10 | 10 |
| Compound No. 1-13 | 0.5 | 0 | 0 | 0 | 0 | 10 | 10 |
|  | 0.25 | 0 | 0 | 0 | 0 | 10 | 10 |
| Compound No. 1-14 | 0.5 | 0 | 0 | 0 | 0 | 10 | 10 |
|  | 0.25 | 0 | 0 | 0 | 0 | 10 | 10 |
| Compound No. 1-15 | 0.5 | 0 | 0 | 0 | 0 | 10 | 10 |
|  | 0.25 | 0 | 0 | 0 | 0 | 10 | 10 |
| Compound No. 1-16 | 0.5 | 0 | 0 | 0 | 0 | 10 | 10 |
|  | 0.25 | 0 | 0 | 0 | 0 | 10 | 10 |
| Compound No. 1-17 | 0.5 | 0 | 0 | 0 | 0 | 10 | 10 |
|  | 0.25 | 0 | 0 | 0 | 0 | 10 | 10 |
| Compound No. 1-18 | 0.5 | 0 | 0 | 0 | 0 | 9 | 10 |
|  | 0.25 | 0 | 0 | 0 | 0 | 5 | 6 |
| Compound No. 1-19 | 0.5 | 0 | 0 | 0 | 0 | 9 | 10 |
|  | 0.25 | 0 | 0 | 0 | 0 | 6 | 6 |
| Compound No. 1-20 | 0.5 | 0 | 0 | 0 | 0 | 8 | 9 |
|  | 0.25 | 0 | 0 | 0 | 0 | 4 | 6 |
| Compound No. 1-21 | 0.5 | 0 | 0 | 0 | 0 | 7 | 8 |
|  | 0.25 | 0 | 0 | 0 | 0 | 3 | 4 |
| Compound No. 1-22 | 0.5 | 0 | 0 | 0 | 0 | 8 | 9 |
|  | 0.25 | 0 | 0 | 0 | 0 | 7 | 7 |
| Compound No. 1-23 | 0.5 | 0 | 0 | 0 | 0 | 10 | 10 |
|  | 0.25 | 0 | 0 | 0 | 0 | 10 | 10 |
| Compound No. 1-24 | 0.5 | 0 | 0 | 0 | 0 | 10 | 10 |
|  | 0.25 | 0 | 0 | 0 | 0 | 10 | 10 |
| Compound No. 1-25 | 0.5 | 0 | 0 | 0 | 0 | 10 | 10 |
|  | 0.25 | 0 | 0 | 0 | 0 | 10 | 10 |
| Compound No. 1-26 | 0.5 | 0 | 0 | 0 | 0 | 10 | 10 |
|  | 0.25 | 0 | 0 | 0 | 0 | 10 | 10 |
| Compound No. 1-27 | 0.5 | 0 | 0 | 0 | 0 | 8 | 8 |
| Reference Compound | 0.5 | 0 | 0 | 0 | 0 | 6 | 6 |

TABLE 1-continued (Test 1-1)
Results of Tests in pre-emergence soil treatments

| Compound No. | Dose active ingredient (kg/ha) | Wh. | Ba. | So. | Ra. | B.G. | Cr.G. |
|---|---|---|---|---|---|---|---|
| (I) | 0.25 | 0 | 0 | 0 | 0 | 1 | 3 |

Wh.: Wheat
So.: Soybean
B.G.: Barnyard Grass (*panicum crus-galli linnaeus*)
Ba.: Barley
Ra.: Radish
Cr.G.: Large Crab Grass (*digitaria sanguinalis scopoli*)

TABLE 2

(Test 1-2)

| Compound No. | Dose active ingredient (kg/ha) | Wh. | Ba. | So. | Ra. | B.G. | Cr.G. |
|---|---|---|---|---|---|---|---|
| Compound No. 2-1 | 0.5 | 0 | 0 | 0 | 0 | 10 | 10 |
|  | 0.25 | 0 | 0 | 0 | 0 | 10 | 10 |
| Compound No. 2-2 | 0.5 | 0 | 0 | 0 | 0 | 10 | 10 |
|  | 0.25 | 0 | 0 | 0 | 0 | 10 | 10 |
| Compound No. 2-3 | 0.5 | 0 | 0 | 0 | 0 | 10 | 10 |
|  | 0.25 | 0 | 0 | 0 | 0 | 10 | 10 |
| Compound No. 2-4 | 0.5 | 0 | 0 | 0 | 0 | 10 | 10 |
|  | 0.25 | 0 | 0 | 0 | 0 | 10 | 10 |
| Compound No. 2-5 | 0.5 | 0 | 0 | 0 | 0 | 10 | 10 |
|  | 0.25 | 0 | 0 | 0 | 0 | 10 | 10 |
| Compound No. 2-6 | 0.5 | 0 | 0 | 0 | 0 | 10 | 10 |
|  | 0.25 | 0 | 0 | 0 | 0 | 10 | 10 |
| Reference Compound (II) | 0.5 | 0 | 0 | 0 | 0 | 2 | 2 |
|  | 0.25 | 0 | 0 | 0 | 0 | 1 | 1 |
| Reference Compound (III) | 0.5 | 0 | 0 | 0 | 0 | 3 | 2 |
|  | 0.25 | 0 | 0 | 0 | 0 | 0 | 1 |
| Reference Compound (IV) | 0.5 | 0 | 0 | 0 | 0 | 1 | 1 |
|  | 0.25 | 0 | 0 | 0 | 0 | 0 | 0 |
| Reference Compound (V) | 0.5 | 0 | 0 | 0 | 0 | 0 | 0 |
|  | 0.25 | 0 | 0 | 0 | 0 | 0 | 0 |

TABLE 3

(Test 1-3)

| Compound No. | Dose active ingredient (kg/ha) | Wh. | Ba. | So. | Ra. | B.G. | Cr.G. |
|---|---|---|---|---|---|---|---|
| Compound No. 3-1 | 0.5 | 0 | 0 | 0 | 0 | 10 | 10 |
|  | 0.25 | 0 | 0 | 0 | 0 | 9 | 10 |
| Compound No. 3-2 | 0.5 | 0 | 0 | 0 | 0 | 10 | 10 |
|  | 0.25 | 0 | 0 | 0 | 0 | 9 | 10 |
| Compound No. 3-3 | 0.5 | 0 | 0 | 0 | 0 | 10 | 10 |
|  | 0.25 | 0 | 0 | 0 | 0 | 9 | 10 |
| Compound No. 3-4 | 0.5 | 0 | 0 | 0 | 0 | 10 | 10 |
|  | 0.25 | 0 | 0 | 0 | 0 | 8 | 10 |
| Compound No. 3-5 | 0.5 | 0 | 0 | 0 | 0 | 10 | 10 |
|  | 0.25 | 0 | 0 | 0 | 0 | 10 | 10 |
| Compound No. 3-6 | 0.5 | 0 | 0 | 0 | 0 | 10 | 10 |
|  | 0.25 | 0 | 0 | 0 | 0 | 9 | 10 |
| Reference Compound (VI) | 0.5 | 0 | 0 | 0 | 0 | 4 | 5 |
|  | 0.25 | 0 | 0 | 0 | 0 | 1 | 3 |
| Reference Compound (VII) | 0.5 | 0 | 0 | 0 | 0 | 3 | 4 |
|  | 0.25 | 0 | 0 | 0 | 0 | 1 | 2 |
| Reference Compound (VIII) | 0.5 | 0 | 0 | 0 | 0 | 4 | 4 |
|  | 0.25 | 0 | 0 | 0 | 0 | 1 | 2 |

TABLE 4

(Test 1-4)

| Compound No. | Dose active ingredient (kg/ha) | Wh. | Ba. | So. | Ra. | B.G. | Cr.G. |
|---|---|---|---|---|---|---|---|
| Compound No. 4-1 | 0.5 | 3 | 4 | 0 | 0 | 10 | 10 |
|  | 0.25 | 1 | 2 | 0 | 0 | 10 | 10 |
| Compound No. 4-2 | 0.5 | 4 | 3 | 0 | 0 | 10 | 10 |
|  | 0.25 | 1 | 0 | 0 | 0 | 10 | 10 |
| Compound No. 4-3 | 0.5 | 0 | 0 | 0 | 0 | 10 | 10 |
|  | 0.25 | 0 | 0 | 0 | 0 | 10 | 10 |
| Compound No. 4-4 | 0.5 | 0 | 2 | 0 | 0 | 10 | 10 |
|  | 0.25 | 0 | 0 | 0 | 0 | 10 | 10 |
| Compound No. 4-5 | 0.5 | 3 | 4 | 0 | 0 | 10 | 10 |
|  | 0.25 | 2 | 2 | 0 | 0 | 10 | 10 |
| Compound No. 4-6 | 0.5 | 0 | 0 | 0 | 0 | 10 | 10 |
|  | 0.25 | 0 | 0 | 0 | 0 | 10 | 10 |
| Compound No. 4-7 | 0.5 | 0 | 0 | 0 | 0 | 10 | 10 |
|  | 0.25 | 0 | 0 | 0 | 0 | 10 | 10 |
| Compound No. 4-8 | 0.5 | 0 | 0 | 0 | 0 | 10 | 10 |
|  | 0.25 | 0 | 0 | 0 | 0 | 10 | 10 |
| Reference Compound (IX) | 0.5 | 2 | 4 | 0 | 0 | 4 | 3 |
|  | 0.25 | 0 | 2 | 0 | 0 | 0 | 0 |
| Reference Compound (X) | 0.5 | 2 | 3 | 0 | 0 | 2 | 4 |
|  | 0.25 | 0 | 2 | 0 | 0 | 0 | 1 |
| Reference Compound (XI) | 0.5 | 2 | 4 | 0 | 0 | 1 | 2 |
|  | 0.25 | 1 | 1 | 0 | 0 | 0 | 0 |
| Reference Compound (XII) | 0.5 | 0 | 2 | 0 | 0 | 3 | 4 |
|  | 0.25 | 0 | 0 | 0 | 0 | 0 | 1 |

TABLE 5

(Test 1-5)

| Compound No. | Dose active ingredient (kg/ha) | Wh. | Ba. | So. | Ra. | B.G. | Cr.G. |
|---|---|---|---|---|---|---|---|
| Compound No. 5-1 | 0.5 | 0 | 0 | 0 | 0 | 9 | 10 |
|  | 0.25 | 0 | 0 | 0 | 0 | 8 | 10 |
| Compound No. 5-2 | 0.5 | 0 | 0 | 0 | 0 | 10 | 10 |
|  | 0.25 | 0 | 0 | 0 | 0 | 9 | 10 |
| Compound No. 5-3 | 0.5 | 0 | 0 | 0 | 0 | 10 | 10 |
|  | 0.25 | 0 | 0 | 0 | 0 | 8 | 10 |
| Compound No. 5-4 | 0.5 | 0 | 0 | 0 | 0 | 10 | 10 |
|  | 0.25 | 0 | 0 | 0 | 0 | 8 | 10 |
| Compound No. 5-5 | 0.5 | 0 | 0 | 0 | 0 | 8 | 10 |
|  | 0.25 | 0 | 0 | 0 | 0 | 7 | 10 |
| Compound No. 5-6 | 0.5 | 0 | 0 | 0 | 0 | 8 | 10 |
|  | 0.25 | 0 | 0 | 0 | 0 | 7 | 10 |
| Compound No. 5-7 | 0.5 | 0 | 0 | 0 | 0 | 8 | 10 |
|  | 0.25 | 0 | 0 | 0 | 0 | 8 | 10 |
| Compound No. 5-8 | 0.5 | 0 | 0 | 0 | 0 | 8 | 7 |
|  | 0.25 | 0 | 0 | 0 | 0 | 4 | 5 |
| Compound No. 5-9 | 0.5 | 0 | 0 | 0 | 0 | 8 | 7 |
|  | 0.25 | 0 | 0 | 0 | 0 | 6 | 5 |
| Compound No. 5-10 | 0.5 | 0 | 0 | 0 | 0 | 8 | 6 |
|  | 0.25 | 0 | 0 | 0 | 0 | 6 | 4 |
| Compound No. 5-11 | 0.5 | 0 | 0 | 0 | 0 | 10 | 10 |
|  | 0.25 | 0 | 0 | 0 | 0 | 10 | 10 |
| Reference Compound (I) | 0.5 | 0 | 0 | 0 | 0 | 4 | 5 |
|  | 0.25 | 0 | 0 | 0 | 0 | 1 | 3 |

TABLE 6

(Test 1-6)

| Compound No. | Dose active ingredient (kg/ha) | Wh. | Ba. | So. | Ra. | B.G. | Cr.G. |
|---|---|---|---|---|---|---|---|
| Compound No. 6-1 | 0.5 | 6 | 7 | 0 | 0 | 10 | 10 |
|  | 0.25 | 3 | 3 | 0 | 0 | 10 | 10 |
| Compound | 0.5 | 5 | 5 | 0 | 0 | 10 | 10 |

TABLE 6-continued (Test 1-6)

| Compound No. | Dose active ingredient (kg/ha) | Wh. | Ba. | So. | Ra. | B.G. | Cr.G. |
|---|---|---|---|---|---|---|---|
| No. 6-2 | 0.25 | 2 | 2 | 0 | 0 | 10 | 10 |
| Compound | 0.5 | 6 | 6 | 0 | 0 | 10 | 10 |
| No. 6-3 | 0.25 | 3 | 3 | 0 | 0 | 10 | 10 |
| Compound | 0.5 | 4 | 6 | 0 | 0 | 10 | 10 |
| No. 6-4 | 0.25 | 2 | 3 | 0 | 0 | 10 | 10 |
| Compound | 6-9 | 3 | 4 | 0 | 0 | 10 | 10 |
| No. 6-5 | 0.25 | 1 | 2 | 0 | 0 | 10 | 10 |
| Compound | 0.5 | 4 | 7 | 0 | 0 | 10 | 10 |
| No. 6-6 | 0.25 | 2 | 3 | 0 | 0 | 10 | 10 |
| Compound | 0.5 | 5 | 6 | 0 | 0 | 10 | 10 |
| No. 6-7 | 0.25 | 2 | 3 | 0 | 0 | 10 | 10 |
| Compound | 0.5 | 3 | 4 | 0 | 0 | 10 | 10 |
| No. 6-8 | 0.25 | 1 | 2 | 0 | 0 | 10 | 10 |
| Compound | 0.5 | 7 | 7 | 0 | 0 | 10 | 10 |
| No. 6-9 | 0.25 | 3 | 3 | 0 | 0 | 10 | 10 |
| Compound | 0.5 | 7 | 6 | 0 | 0 | 10 | 10 |
| No. 6-10 | 0.25 | 3 | 3 | 0 | 0 | 10 | 10 |
| Compound | 0.5 | 5 | 4 | 0 | 0 | 10 | 10 |
| No. 6-11 | 0.25 | 2 | 2 | 0 | 0 | 10 | 10 |
| Compound | 0.5 | 4 | 6 | 0 | 0 | 10 | 10 |
| No. 6-12 | 0.25 | 2 | 3 | 0 | 0 | 10 | 10 |
| Compound | 0.5 | 7 | 7 | 0 | 0 | 10 | 10 |
| No. 6-13 | 0.25 | 3 | 3 | 0 | 0 | 10 | 10 |
| Compound | 0.5 | 6 | 5 | 0 | 0 | 10 | 10 |
| No. 6-14 | 0.25 | 3 | 2 | 0 | 0 | 10 | 10 |
| Compound | 0.5 | 6 | 4 | 0 | 0 | 10 | 10 |
| No. 6-15 | 0.25 | 2 | 1 | 0 | 0 | 10 | 10 |
| Compound | 0.5 | 6 | 6 | 0 | 0 | 10 | 10 |
| No. 6-16 | 0.25 | 3 | 3 | 0 | 0 | 0 | 10 |
| Compound | 0.5 | 6 | 5 | 0 | 0 | 10 | 10 |
| No. 6-17 | 0.25 | 3 | 2 | 0 | 0 | 10 | 10 |
| Compound | 0.5 | 0 | 0 | 0 | 0 | 10 | 10 |
| No. 6-18 | 0.25 | 0 | 0 | 0 | 0 | 10 | 10 |
| Reference Compound (XIII) | 0.5 | 0 | 0 | 0 | 0 | 0 | 0 |
| | 0.25 | 0 | 0 | 0 | 0 | 0 | 0 |
| Reference Compound (I) | 0.5 | 0 | 0 | 0 | 0 | 0 | 0 |
| | 0.25 | 0 | 0 | 0 | 0 | 0 | 0 |
| Reference Compound (VI) | 0.5 | 0 | 0 | 0 | 0 | 5 | 6 |
| | 0.25 | 0 | 0 | 0 | 0 | 1 | 2 |
| Reference Compound (XIV) | 0.5 | 0 | 0 | 0 | 0 | 4 | 4 |
| | 0.25 | 0 | 0 | 0 | 0 | 0 | 1 |
| Reference Compound (XV) | 0.5 | 2 | 1 | 0 | 0 | 10 | 10 |
| | 0.25 | 0 | 0 | 0 | 0 | 6 | 5 |

TABLE 7

(Test 1-7)

| Compound No. | Dose active ingredient (kg/ha) | Wh. | Ba. | So. | Ra. | B.G. | Cr.G. |
|---|---|---|---|---|---|---|---|
| Compound No. 7-1 | 0.5 | 10 | 10 | 0 | 0 | 10 | 10 |
| | 0.25 | 10 | 7 | 0 | 0 | 10 | 10 |
| Compound No. 7-2 | 0.5 | 10 | 10 | 0 | 0 | 10 | 10 |
| | 0.25 | 10 | 6 | 0 | 0 | 10 | 10 |
| Compound No. 7-3 | 0.5 | 10 | 10 | 0 | 0 | 10 | 10 |
| | 0.25 | 8 | 5 | 0 | 0 | 10 | 10 |
| Compound No. 7-4 | 0.5 | 10 | 10 | 0 | 0 | 10 | 10 |
| | 0.25 | 10 | 7 | 0 | 0 | 10 | 10 |
| Reference Compound (XVI) | 0.5 | 2 | 3 | 0 | 0 | 2 | 3 |
| | 0.25 | 0 | 0 | 0 | 0 | 0 | 1 |
| Reference Compound (XVII) | 0.5 | 0 | 0 | 0 | 0 | 0 | 1 |
| | 0.25 | 0 | 0 | 0 | 0 | 0 | 0 |

TABLE 8

(Test 1-8)

| Compound No. | Dose active ingredient (kg/ha) | Wh. | Ba. | So. | Ra. | B.G. | Cr.G. |
|---|---|---|---|---|---|---|---|
| Compound No. 8-1 | 0.5 | 0 | 0 | 0 | 0 | 10 | 10 |
| | 0.25 | 0 | 0 | 0 | 0 | 10 | 10 |
| Compound No. 8-2 | 0.5 | 0 | 0 | 0 | 0 | 10 | 10 |
| | 0.25 | 0 | 0 | 0 | 0 | 10 | 10 |
| Compound No. 8-3 | 0.5 | 0 | 0 | 0 | 0 | 10 | 10 |
| | 0.25 | 0 | 0 | 0 | 0 | 10 | 10 |
| Compound No. 8-4 | 0.5 | 0 | 0 | 0 | 0 | 10 | 10 |
| | 0.25 | 0 | 0 | 0 | 0 | 10 | 10 |
| Compound No. 8-5 | 0.5 | 0 | 0 | 0 | 0 | 10 | 10 |
| | 0.25 | 0 | 0 | 0 | 0 | 10 | 10 |
| Compound No. 8-6 | 0.5 | 0 | 0 | 0 | 0 | 10 | 10 |
| | 0.25 | 0 | 0 | 0 | 0 | 10 | 10 |

TABLE 9

(Test 1-9)

| Compound No. | Dose active ingredient (kg/ha) | Wh. | Ba. | So. | Ra. | B.G. | Cr.G. |
|---|---|---|---|---|---|---|---|
| Compound No. 9-1 | 0.5 | 0 | 0 | 0 | 0 | 10 | 10 |
| | 0.25 | 0 | 0 | 0 | 0 | 10 | 10 |
| Compound No. 9-2 | 0.5 | 0 | 0 | 0 | 0 | 10 | 10 |
| | 0.25 | 0 | 0 | 0 | 0 | 10 | 10 |
| Compound No. 9-3 | 0.5 | 0 | 0 | 0 | 0 | 10 | 10 |
| | 0.25 | 0 | 0 | 0 | 0 | 10 | 10 |
| Compound No. 9-4 | 0.5 | 0 | 0 | 0 | 0 | 10 | 10 |
| | 0.25 | 0 | 0 | 0 | 0 | 10 | 10 |
| Compound No. 9-5 | 0.5 | 0 | 0 | 0 | 0 | 10 | 10 |
| | 0.25 | 0 | 0 | 0 | 0 | 10 | 10 |
| Compound No. 9-6 | 0.5 | 0 | 0 | 0 | 0 | 10 | 10 |
| | 0.25 | 0 | 0 | 0 | 0 | 10 | 10 |

EXPERIMENT 2

Test for crop plants and up-land weeds in pre-emergence soil treatment.

Each polyethylene pot of 2,000 cm² was filled with up-land soil and seeds of rice, maize, wheat, soybean, cotton, radish, barnyard grass, large crab grass, dent foxtail, johnson grass and goose foot (25 seeds for each plant) were sown in a depth of 0.5 cm.

Each emulsifiable concentrate prepared in accordance with the method of Composition No. 2 was diluted with water to give 0.25, 0.125 and 0.625 Kg/ha. of the active ingredient, and the diluted solution was uniformly sprayed on the surface of the soil at a rate of 20.0 ml per one pot.

Twenty days after the treatment, the herbicidal effect and the phytotoxicity of the crop plants were observed and rated as described above.

| | |
|---|---|
| Ric.: | Rice |
| Mai.: | Maize |
| Wh.: | Wheat |
| So.: | Soybean |
| Cot.: | Cotton |
| Ra.: | Radish |
| B.G.: | Barnyard Grass (*panicum crus-galli linnaeus*) |
| Cr.G.: | Large Crab Grass (*digitaria sanguinalis scopoli*) |
| D.F.: | Dent Foxtail (*alopecurus aequalis sobolewski* var. *amurensis ohwi*) |
| J.G.: | Johnson Grass (*sorghum halepense*) |
| G.F.: | Goose Foot (*chenopodium album linnaeus* var. *centrorubrum makino*) |

The experiments were separately carried out as stated in Tables.

TABLE 10

(Test 2-1)

| Compound No. | Dose active ingredient (kg/ha) | Ric. | Mai. | Wh. | So. | Cot. | Ra. | B.G. | Cr.G. | D.F. | J.G. | G.F. |
|---|---|---|---|---|---|---|---|---|---|---|---|---|
| Compound No. 1-3 | 0.25 | 6 | 4 | 0 | 0 | 0 | 0 | 10 | 10 | 10 | 10 | 0 |
|  | 0.125 | 4 | 1 | 0 | 0 | 0 | 0 | 8 | 10 | 10 | 10 | 0 |
|  | 0.0625 | 1 | 0 | 0 | 0 | 0 | 0 | 6 | 7 | 8 | 8 | 0 |
| Compound No. 1-8 | 0.25 | 7 | 5 | 0 | 0 | 0 | 0 | 10 | 10 | 10 | 10 | 0 |
|  | 0.125 | 5 | 1 | 0 | 0 | 0 | 0 | 9 | 9 | 10 | 10 | 0 |
|  | 0.0625 | 2 | 0 | 0 | 0 | 0 | 0 | 6 | 7 | 9 | 7 | 0 |
| Compound No. 1-9 | 0.25 | 6 | 4 | 0 | 0 | 0 | 0 | 10 | 10 | 10 | 10 | 0 |
|  | 0.125 | 4 | 1 | 0 | 0 | 0 | 0 | 9 | 10 | 10 | 10 | 0 |
|  | 0.0625 | 2 | 0 | 0 | 0 | 0 | 0 | 7 | 7 | 8 | 8 | 0 |
| Compound No. 1-10 | 0.25 | 5 | 3 | 0 | 0 | 0 | 0 | 10 | 10 | 10 | 10 | 0 |
|  | 0.125 | 4 | 1 | 0 | 0 | 0 | 0 | 8 | 9 | 9 | 10 | 0 |
|  | 0.0625 | 1 | 0 | 0 | 0 | 0 | 0 | 6 | 7 | 9 | 9 | 0 |
| Compound No. 1-15 | 0.25 | 4 | 3 | 0 | 0 | 0 | 0 | 10 | 10 | 10 | 10 | 0 |
|  | 0.125 | 2 | 0 | 0 | 0 | 0 | 0 | 7 | 8 | 10 | 8 | 0 |
|  | 0.0625 | 0 | 0 | 0 | 0 | 0 | 0 | 5 | 6 | 8 | 8 | 0 |
| Compound No. 1-24 | 0.25 | 6 | 4 | 0 | 0 | 0 | 0 | 10 | 10 | 10 | 10 | 0 |
|  | 0.125 | 4 | 1 | 0 | 0 | 0 | 0 | 9 | 9 | 10 | 10 | 0 |
|  | 0.0625 | 1 | 0 | 0 | 0 | 0 | 0 | 7 | 7 | 8 | 8 | 0 |
| Compound No. 1-25 | 0.25 | 6 | 4 | 0 | 0 | 0 | 0 | 10 | 10 | 10 | 10 | 0 |
|  | 0.125 | 4 | 1 | 0 | 0 | 0 | 0 | 8 | 9 | 10 | 9 | 0 |
|  | 0.0625 | 2 | 0 | 0 | 0 | 0 | 0 | 6 | 6 | 9 | 7 | 0 |
| Compound No. 1-26 | 0.25 | 5 | 3 | 0 | 0 | 0 | 0 | 10 | 10 | 10 | 10 | 0 |
|  | 0.125 | 3 | 1 | 0 | 0 | 0 | 0 | 8 | 8 | 9 | 9 | 0 |
|  | 0.0625 | 1 | 0 | 0 | 0 | 0 | 0 | 6 | 6 | 7 | 7 | 0 |
| Reference Compound (XXIII) | 0.25 | 0 | 0 | 0 | 0 | 0 | 0 | 2 | 3 | 2 | 0 | 0 |
|  | 0.125 | 0 | 0 | 0 | 0 | 0 | 0 | 0 | 0 | 0 | 0 | 0 |
|  | 0.0625 | 0 | 0 | 0 | 0 | 0 | 0 | 0 | 0 | 0 | 0 | 0 |
| Reference Compound (XXIV) | 0.25 | 0 | 0 | 0 | 0 | 0 | 0 | 1 | 2 | 1 | 0 | 0 |
|  | 0.125 | 0 | 0 | 0 | 0 | 0 | 0 | 0 | 0 | 0 | 0 | 0 |
|  | 0.0625 | 0 | 0 | 0 | 0 | 0 | 0 | 0 | 0 | 0 | 0 | 0 |

TABLE 11

(Test 2-2)

| Compound No. | Dose active ingredient (kg/ha) | Ric. | Mai. | Wh. | So. | Cot. | Ra. | B.G. | Cr.G. | D.F. | J.G. | G.F. |
|---|---|---|---|---|---|---|---|---|---|---|---|---|
| Compound No. 2-1 | 0.25 | 3 | 4 | 0 | 0 | 0 | 0 | 10 | 10 | 10 | 10 | 0 |
|  | 0.125 | 0 | 0 | 0 | 0 | 0 | 0 | 10 | 10 | 10 | 9 | 0 |
| Compound No. 2-2 | 0.25 | 3 | 4 | 0 | 0 | 0 | 0 | 10 | 10 | 10 | 10 | 0 |
|  | 0.125 | 0 | 0 | 0 | 0 | 0 | 0 | 10 | 10 | 10 | 10 | 0 |
| Compound No. 2-3 | 0.25 | 3 | 3 | 0 | 0 | 0 | 0 | 10 | 10 | 10 | 10 | 0 |
|  | 0.125 | 0 | 0 | 0 | 0 | 0 | 0 | 10 | 10 | 10 | 8 | 0 |
| Compound No. 2-4 | 0.25 | 3 | 3 | 0 | 0 | 0 | 0 | 10 | 10 | 10 | 10 | 0 |
|  | 0.125 | 0 | 0 | 0 | 0 | 0 | 0 | 10 | 9 | 10 | 9 | 0 |
| Compound No. 2-5 | 0.25 | 3 | 3 | 0 | 0 | 0 | 0 | 10 | 10 | 10 | 10 | 0 |
|  | 0.125 | 0 | 0 | 0 | 0 | 0 | 0 | 10 | 8 | 9 | 7 | 0 |
| Compound No. 2-6 | 0.25 | 3 | 3 | 0 | 0 | 0 | 0 | 10 | 10 | 10 | 10 | 0 |
|  | 0.125 | 0 | 0 | 0 | 0 | 0 | 0 | 10 | 10 | 9 | 7 | 0 |
| Reference Compound (II) | 0.25 | 2 | 3 | 0 | 0 | 0 | 0 | 6 | 4 | 3 | 2 | 0 |
|  | 0.125 | 1 | 0 | 0 | 0 | 0 | 0 | 1 | 0 | 0 | 0 | 0 |
| Reference Compound (III) | 0.25 | 2 | 4 | 0 | 0 | 0 | 0 | 5 | 5 | 4 | 1 | 0 |
|  | 0.125 | 0 | 1 | 0 | 0 | 0 | 0 | 0 | 2 | 1 | 0 | 0 |
| Reference Compound (IV) | 0.25 | 2 | 3 | 0 | 0 | 0 | 0 | 3 | 4 | 5 | 2 | 0 |
|  | 0.125 | 0 | 1 | 0 | 0 | 0 | 0 | 0 | 0 | 1 | 0 | 0 |
| Reference Compound (V) | 0.25 | 3 | 3 | 0 | 0 | 0 | 0 | 1 | 2 | 4 | 1 | 0 |
|  | 0.125 | 0 | 0 | 0 | 0 | 0 | 0 | 0 | 0 | 0 | 0 | 0 |

TABLE 12

(Test 2-3)

| Compound No. | Dose active ingredient (kg/ha) | Ric. | Mai. | Wh. | So. | Cot. | Ra. | B.G. | Cr.G. | D.F. | J.G. | G.F. |
|---|---|---|---|---|---|---|---|---|---|---|---|---|
| Compound No. 4-1 | 0.25 | 5 | 8 | 3 | 0 | 0 | 0 | 10 | 10 | 10 | 10 | 0 |
|  | 0.125 | 3 | 6 | 2 | 0 | 0 | 0 | 10 | 10 | 10 | 10 | 0 |
|  | 0.0625 | 0 | 2 | 0 | 0 | 0 | 0 | 10 | 10 | 10 | 7 | 0 |
| Compound No. 4-2 | 0.25 | 6 | 8 | 3 | 0 | 0 | 0 | 10 | 10 | 10 | 10 | 0 |
|  | 0.125 | 3 | 7 | 1 | 0 | 0 | 0 | 10 | 10 | 10 | 10 | 0 |
|  | 0.0625 | 0 | 3 | 0 | 0 | 0 | 0 | 10 | 10 | 10 | 5 | 0 |

TABLE 12-continued (Test 2-3)

| Compound No. | Dose active ingredient (kg/ha) | Ric. | Mai. | Wh. | So. | Cot. | Ra. | B.G. | Cr.G. | D.F. | J.G. | G.F. |
|---|---|---|---|---|---|---|---|---|---|---|---|---|
| Compound No. 4-3 | 0.25 | 2 | 3 | 0 | 0 | 0 | 0 | 10 | 10 | 10 | 10 | 0 |
|  | 0.125 | 0 | 0 | 0 | 0 | 0 | 0 | 10 | 10 | 10 | 10 | 0 |
|  | 0.0625 | 0 | 0 | 0 | 0 | 0 | 0 | 10 | 10 | 10 | 6 | 0 |
| Compound No. 4-4 | 0.25 | 1 | 1 | 0 | 0 | 0 | 0 | 10 | 10 | 10 | 10 | 0 |
|  | 0.125 | 0 | 0 | 0 | 0 | 0 | 0 | 10 | 10 | 10 | 10 | 0 |
|  | 0.0625 | 0 | 0 | 0 | 0 | 0 | 0 | 10 | 10 | 10 | 8 | 0 |
| Compound No. 4-5 | 0.25 | 6 | 7 | 3 | 0 | 0 | 0 | 10 | 10 | 10 | 10 | 0 |
|  | 0.125 | 2 | 5 | 1 | 0 | 0 | 0 | 10 | 10 | 10 | 9 | 0 |
|  | 0.0625 | 0 | 1 | 0 | 0 | 0 | 0 | 7 | 8 | 7 | 7 | 0 |
| Compound No. 4-6 | 0.25 | 1 | 1 | 0 | 0 | 0 | 0 | 10 | 10 | 10 | 10 | 0 |
|  | 0.125 | 0 | 0 | 0 | 0 | 0 | 0 | 10 | 10 | 10 | 10 | 0 |
|  | 0.0625 | 0 | 0 | 0 | 0 | 0 | 0 | 8 | 7 | 7 | 6 | 0 |
| Compound No. 4-7 | 0.25 | 1 | 1 | 0 | 0 | 0 | 0 | 10 | 10 | 10 | 10 | 0 |
|  | 0.125 | 0 | 0 | 0 | 0 | 0 | 0 | 10 | 10 | 10 | 10 | 0 |
|  | 0.0625 | 0 | 0 | 0 | 0 | 0 | 0 | 7 | 10 | 8 | 6 | 0 |
| Compound No. 4-8 | 0.25 | 0 | 1 | 0 | 0 | 0 | 0 | 10 | 10 | 10 | 10 | 0 |
|  | 0.125 | 0 | 0 | 0 | 0 | 0 | 0 | 10 | 10 | 10 | 10 | 0 |
|  | 0.0625 | 0 | 0 | 0 | 0 | 0 | 0 | 10 | 10 | 8 | 6 | 0 |
| Reference Compound (IX) | 0.25 | 0 | 0 | 0 | 0 | 0 | 0 | 1 | 3 | 2 | 1 | 0 |
|  | 0.125 | 0 | 0 | 0 | 0 | 0 | 0 | 0 | 1 | 0 | 0 | 0 |
|  | 0.0625 | 0 | 0 | 0 | 0 | 0 | 0 | 0 | 0 | 0 | 0 | 0 |
| Reference Compound (XI) | 0.25 | 0 | 0 | 0 | 0 | 0 | 0 | 0 | 0 | 2 | 0 | 0 |
|  | 0.125 | 0 | 0 | 0 | 0 | 0 | 0 | 0 | 0 | 0 | 0 | 0 |
|  | 0.0625 | 0 | 0 | 0 | 0 | 0 | 0 | 0 | 0 | 0 | 0 | 0 |

EXPERIMENT 3

Test for crop plants and up-land weeds in (post-emergence germination) foliage treatment.

Each pot of 600 cm$^2$ was filled with up-land soil and seeds of corn, barley, soybean, radish, barnyard grass and large crab grass were sown.

Each emulsifiable concentrate prepared in accordance with the method of Composition No. 2 was diluted with water to give the specific concentration of the compound and the diluted solution was uniformly sprayed at a rate of 1 kl/ha, when the gramineous weeds were grown to 2 to 2.5 leaf stage and the broad-leaf weeds were grown to the first divergence stage.

Fifteen days from the treatment, the herbicidal effect and the phytotoxicity of the crop plants were observed and rated as described above.

| | |
|---|---|
| Wh.: | Wheat |
| Ba.: | Barley |
| So.: | Soybean |
| Ra.: | Radish |
| B.G.: | Barnyard Grass (*panicum crus-galli linnaeus*) |
| Cr.G.: | Large Crab Grass (*digitaria sanguinalis scopoli*) |

The experiments were separately carried out as stated in Tables.

TABLE 13

(Test 3-1)

| Compound No. | Concentration (ppm) | Wh. | Ba. | So. | Ra. | B.G. | Cr.G. |
|---|---|---|---|---|---|---|---|
| Compound No. 1-1 | 500 | 0 | 0 | 0 | 0 | 10 | 10 |
|  | 200 | 0 | 0 | 0 | 0 | 10 | 10 |
| Compound No. 1-2 | 500 | 0 | 0 | 0 | 0 | 10 | 10 |
|  | 250 | 0 | 0 | 0 | 0 | 10 | 10 |
| Compound No. 1-3 | 500 | 0 | 0 | 0 | 0 | 10 | 10 |
|  | 250 | 0 | 0 | 0 | 0 | 10 | 10 |
| Compound No. 1-4 | 500 | 0 | 0 | 0 | 0 | 10 | 10 |
|  | 250 | 0 | 0 | 0 | 0 | 10 | 10 |
| Compound No. 1-5 | 500 | 0 | 0 | 0 | 0 | 8 | 7 |
| Compound No. 1-6 | 250 | 0 | 0 | 0 | 0 | 5 | 5 |
|  | 500 | 0 | 0 | 0 | 0 | 10 | 10 |
| Compound No. 1-7 | 250 | 0 | 0 | 0 | 0 | 10 | 10 |
|  | 500 | 0 | 0 | 0 | 0 | 10 | 10 |
| Compound No. 1-8 | 250 | 0 | 0 | 0 | 0 | 10 | 10 |
|  | 500 | 0 | 0 | 0 | 0 | 10 | 10 |
| Compound No. 1-9 | 250 | 0 | 0 | 0 | 0 | 10 | 10 |
|  | 500 | 0 | 0 | 0 | 0 | 10 | 10 |
| Compound No. 1-10 | 250 | 0 | 0 | 0 | 0 | 10 | 10 |
|  | 500 | 0 | 0 | 0 | 0 | 10 | 10 |
| Compound No. 1-11 | 250 | 0 | 0 | 0 | 0 | 10 | 10 |
|  | 500 | 0 | 0 | 0 | 0 | 10 | 10 |
| Compound No. 1-12 | 250 | 0 | 0 | 0 | 0 | 10 | 10 |
|  | 500 | 0 | 0 | 0 | 0 | 10 | 10 |
| Compound No. 1-13 | 250 | 0 | 0 | 0 | 0 | 10 | 10 |
|  | 500 | 0 | 0 | 0 | 0 | 10 | 10 |
| Compound No. 1-14 | 250 | 0 | 0 | 0 | 0 | 10 | 10 |
|  | 500 | 0 | 0 | 0 | 0 | 10 | 10 |
| Compound No. 1-15 | 250 | 0 | 0 | 0 | 0 | 10 | 10 |
|  | 500 | 0 | 0 | 0 | 0 | 10 | 10 |
| Compound No. 1-16 | 250 | 0 | 0 | 0 | 0 | 10 | 10 |
|  | 500 | 0 | 0 | 0 | 0 | 10 | 10 |
| Compound No. 1-17 | 250 | 0 | 0 | 0 | 0 | 10 | 10 |
|  | 500 | 0 | 0 | 0 | 0 | 7 | 7 |
| Compound No. 1-18 | 250 | 0 | 0 | 0 | 0 | 4 | 5 |
|  | 500 | 0 | 0 | 0 | 0 | 7 | 7 |
| Compound No. 1-19 | 250 | 0 | 0 | 0 | 0 | 4 | 5 |
|  | 500 | 0 | 0 | 0 | 0 | 7 | 6 |
| Compound No. 1-20 | 250 | 0 | 0 | 0 | 0 | 3 | 4 |
|  | 500 | 0 | 0 | 0 | 0 | 7 | 6 |
| Compound No. 1-21 | 250 | 0 | 0 | 0 | 0 | 3 | 4 |
|  | 500 | 0 | 0 | 0 | 0 | 7 | 7 |
| Compound No. 1-22 | 250 | 0 | 0 | 0 | 0 | 6 | 6 |
|  | 500 | 0 | 0 | 0 | 0 | 10 | 10 |
| Compound No. 1-23 | 250 | 0 | 0 | 0 | 0 | 10 | 10 |
|  | 500 | 0 | 0 | 0 | 0 | 10 | 10 |
| Compound No. 1-24 | 250 | 0 | 0 | 0 | 0 | 10 | 10 |
|  | 500 | 0 | 0 | 0 | 0 | 10 | 10 |
| Compound No. 1-25 | 250 | 0 | 0 | 0 | 0 | 10 | 10 |
|  | 500 | 0 | 0 | 0 | 0 | 10 | 10 |
| Compound No. 1-26 | 250 | 0 | 0 | 0 | 0 | 10 | 10 |
|  | 500 | 0 | 0 | 0 | 0 | 10 | 10 |
| Compound No. 1-27 | 250 | 0 | 0 | 0 | 0 | 7 | 6 |
| Reference Compound | 500 | 0 | 0 | 0 | 0 | 4 | 5 |

TABLE 13-continued (Test 3-1)

| Compound No. | Concentration (ppm) | Wh. | Ba. | So. | Ra. | B.G. | Cr.G. |
| --- | --- | --- | --- | --- | --- | --- | --- |
| (I) | 250 | 0 | 0 | 0 | 0 | 1 | 2 |

TABLE 14

(Test 3-2)

| Compound No. | Concentration (ppm) | Wh. | Ba. | So. | Ra. | B.G. | Cr.G. |
| --- | --- | --- | --- | --- | --- | --- | --- |
| Compound No. 2-1 | 500 | 0 | 0 | 0 | 0 | 10 | 10 |
| | 250 | 0 | 0 | 0 | 0 | 10 | 10 |
| Compound No. 2-2 | 500 | 0 | 0 | 0 | 0 | 10 | 10 |
| | 250 | 0 | 0 | 0 | 0 | 10 | 10 |
| Compound No. 2-3 | 500 | 0 | 0 | 0 | 0 | 10 | 10 |
| | 250 | 0 | 0 | 0 | 0 | 10 | 10 |
| Compound No. 2-4 | 500 | 0 | 0 | 0 | 0 | 10 | 10 |
| | 250 | 0 | 0 | 0 | 0 | 10 | 10 |
| Compound No. 2-5 | 500 | 0 | 0 | 0 | 0 | 10 | 10 |
| | 250 | 0 | 0 | 0 | 0 | 10 | 10 |
| Compound No. 2-6 | 500 | 0 | 0 | 0 | 0 | 10 | 10 |
| | 250 | 0 | 0 | 0 | 0 | 10 | 10 |
| Reference Compound (II) | 500 | 0 | 0 | 0 | 0 | 4 | 2 |
| | 250 | 0 | 0 | 0 | 0 | 1 | 1 |
| Reference Compound (III) | 500 | 0 | 0 | 0 | 0 | 2 | 0 |
| | 250 | 0 | 0 | 0 | 0 | 0 | 0 |
| Reference Compound (IV) | 500 | 0 | 0 | 0 | 0 | 4 | 2 |
| | 250 | 0 | 0 | 0 | 0 | 1 | 0 |
| Reference Compound (V) | 500 | 0 | 0 | 0 | 0 | 0 | 0 |
| | 250 | 0 | 0 | 0 | 0 | 0 | 0 |

The diluted solution was applied when the gramineous weeds were grown to 3.0 to 3.5 leaf stage.
The other conditions were the same.

TABLE 15

(Test 3-3)

| Compound No. | Concentration (ppm) | Wh. | Ba. | So. | Ra. | B.G. | Cr.G. |
| --- | --- | --- | --- | --- | --- | --- | --- |
| Compound No. 4-1 | 500 | 2 | 2 | 0 | 0 | 10 | 10 |
| | 250 | 0 | 1 | 0 | 0 | 10 | 10 |
| Compound No. 4-2 | 500 | 10 | 9 | 0 | 0 | 10 | 10 |
| | 250 | 6 | 8 | 0 | 0 | 10 | 10 |
| Compound No. 4-3 | 500 | 0 | 0 | 0 | 0 | 10 | 10 |
| | 250 | 0 | 0 | 0 | 0 | 10 | 10 |
| Compound No. 4-4 | 500 | 0 | 1 | 0 | 0 | 10 | 10 |
| | 250 | 0 | 0 | 0 | 0 | 10 | 10 |
| Compound No. 4-5 | 500 | 4 | 6 | 0 | 0 | 10 | 10 |
| | 250 | 3 | 4 | 0 | 0 | 10 | 10 |
| Compound No. 4-6 | 500 | 0 | 0 | 0 | 0 | 10 | 10 |
| | 250 | 0 | 0 | 0 | 0 | 9 | 10 |
| Compound No. 4-7 | 500 | 0 | 0 | 0 | 0 | 10 | 10 |
| | 250 | 0 | 0 | 0 | 0 | 10 | 10 |
| Compound No. 4-8 | 500 | 0 | 0 | 0 | 0 | 10 | 10 |
| | 250 | 0 | 0 | 0 | 0 | 10 | 9 |
| Reference Compound (IX) | 500 | 0 | 0 | 0 | 0 | 2 | 3 |
| | 250 | 0 | 0 | 0 | 0 | 0 | 0 |
| Reference Compound (X) | 500 | 0 | 0 | 0 | 0 | 3 | 4 |
| | 250 | 0 | 0 | 0 | 0 | 1 | 2 |
| Reference Compound (XI) | 500 | 0 | 0 | 0 | 0 | 0 | 0 |
| | 250 | 0 | 0 | 0 | 0 | 0 | 0 |
| Reference Compound (XII) | 500 | 0 | 0 | 0 | 0 | 1 | 2 |
| | 250 | 0 | 0 | 0 | 0 | 0 | 0 |

The diluted solution was applied when the gramineous weeds were grown to 3.0 to 3.5 leaf stage.
The other conditions were the same.

TABLE 16

(Test 3-4)

| Compound No. | Concentration (ppm) | Wh. | Ba. | So. | Ra. | B.G. | Cr.G. |
| --- | --- | --- | --- | --- | --- | --- | --- |
| Compound No. 8-1 | 500 | 0 | 0 | 0 | 0 | 10 | 10 |
| | 250 | 0 | 0 | 0 | 0 | 10 | 10 |
| Compound No. 8-2 | 500 | 0 | 0 | 0 | 0 | 10 | 10 |
| | 250 | 0 | 0 | 0 | 0 | 10 | 10 |
| Reference Compound (XVIII) | 500 | 8 | 9 | 0 | 0 | 9 | 8 |
| | 250 | 6 | 7 | 0 | 0 | 7 | 6 |
| Reference Compound (XIX) | 500 | 7 | 8 | 0 | 0 | 9 | 8 |
| | 250 | 4 | 6 | 0 | 0 | 7 | 6 |
| Reference Compound (XX) | 500 | 9 | 10 | 0 | 0 | 10 | 8 |
| | 250 | 7 | 6 | 0 | 0 | 7 | 5 |
| Reference Compound (XXI) | 500 | 8 | 9 | 0 | 0 | 10 | 10 |
| | 250 | 5 | 6 | 0 | 0 | 7 | 6 |
| Reference Compound (XXII) | 500 | 7 | 7 | 0 | 0 | 10 | 10 |
| | 250 | 5 | 5 | 0 | 0 | 8 | 7 |

EXPERIMENT 4

Test for crop plants and up-land weeds in post-emergence foliage treatment.

Each polyethylene pot of 2,000 cm² was filled with up-land soil and seeds of rice, maize, wheat, soybean, cotton, radish, barn-yard grass, crab grass, dent foxtail, johnson grass and goose foot (25 seeds for each plant) were sown.

Each emulsifiable concentrate prepared in accordance with the method of Composition No. 2 was diluted with water to give the concentration of 125, 62.5 and 31.25 ppm and the diluted solution was uniformly sprayed at a rate of 20.0 ml per pot, when the plants were grown to 2 to 4 leaf stages.

Ten days from the treatment, the herbicidal effect and the phytotoxicity of the crop plants were observed and rated as described above.

| | |
| --- | --- |
| Ric: | Rice |
| Mai.: | Maize |
| Wh.: | Wheat |
| So.: | Soybean |
| Cot.: | Cotton |
| Ra.: | Radish |
| B.G.: | Barnyard Grass (*panicum crus-galli linnaeus*) |
| Cr.G.: | Large Crab Grass (*digitaria sanguinalis scopoli*) |
| D.F.: | Dent Foxtail (*alopecurus aequalis sobolewski* var. *amurensis ohwi*) |
| J.G.: | Johnson Grass (*sorghum halepense*) |
| G.F.: | Goose Foot (*chenopodium album linnaeus* var. *centrorubrum makino*) |

In Test 4-2, twenty days from the treatment, the herbicidal effect and the phytotoxicity of the crop plants were observed.

TABLE 17

(Test 4-1)

| Compound No. | Concentration (ppm) | Ric. | Mai. | Wh. | So. | Cot. | Ra. | B.G. | Cr.G. | D.F. | J.G. | G.F. |
|---|---|---|---|---|---|---|---|---|---|---|---|---|
| Compound No. 1-3 | 125 | 3 | 0 | 0 | 0 | 0 | 0 | 10 | 10 | 10 | 10 | 0 |
| | 62.5 | 0 | 0 | 0 | 0 | 0 | 0 | 10 | 10 | 10 | 10 | 0 |
| | 31.25 | 0 | 0 | 0 | 0 | 0 | 0 | 6 | 8 | 9 | 8 | 0 |
| Compound No. 1-8 | 125 | 6 | 5 | 0 | 0 | 0 | 0 | 10 | 10 | 10 | 10 | 0 |
| | 62.5 | 2 | 2 | 0 | 0 | 0 | 0 | 10 | 10 | 10 | 10 | 0 |
| | 31.25 | 0 | 0 | 0 | 0 | 0 | 0 | 8 | 10 | 10 | 9 | 0 |
| Compound No. 1-9 | 125 | 6 | 5 | 0 | 0 | 0 | 0 | 10 | 10 | 10 | 10 | 0 |
| | 62.5 | 2 | 2 | 0 | 0 | 0 | 0 | 10 | 10 | 10 | 10 | 0 |
| | 31.25 | 0 | 0 | 0 | 0 | 0 | 0 | 9 | 10 | 9 | 9 | 0 |
| Compound No. 1-10 | 125 | 5 | 5 | 0 | 0 | 0 | 0 | 10 | 10 | 10 | 10 | 0 |
| | 62.5 | 1 | 1 | 0 | 0 | 0 | 0 | 10 | 10 | 10 | 10 | 0 |
| | 31.25 | 0 | 0 | 0 | 0 | 0 | 0 | 8 | 10 | 9 | 9 | 0 |
| Compound No. 1-15 | 125 | 4 | 3 | 0 | 0 | 0 | 0 | 10 | 10 | 10 | 10 | 0 |
| | 62.5 | 0 | 0 | 0 | 0 | 0 | 0 | 8 | 8 | 8 | 8 | 0 |
| | 31.25 | 0 | 0 | 0 | 0 | 0 | 0 | 5 | 6 | 6 | 7 | 0 |
| Compound No. 1-24 | 125 | 0 | 4 | 0 | 0 | 0 | 0 | 10 | 10 | 10 | 8 | 0 |
| | 62.5 | 0 | 1 | 0 | 0 | 0 | 0 | 10 | 9 | 8 | 7 | 0 |
| | 31.25 | 0 | 0 | 0 | 0 | 0 | 0 | 7 | 8 | 7 | 6 | 0 |
| Compound No. 1-25 | 125 | 0 | 4 | 0 | 0 | 0 | 0 | 10 | 10 | 10 | 8 | 0 |
| | 62.5 | 0 | 1 | 0 | 0 | 0 | 0 | 10 | 9 | 8 | 7 | 0 |
| | 31.25 | 0 | 0 | 0 | 0 | 0 | 0 | 8 | 7 | 0 | 5 | 0 |
| Compound No. 1-26 | 125 | 0 | 3 | 0 | 0 | 0 | 0 | 10 | 10 | 10 | 8 | 0 |
| | 62.5 | 0 | 1 | 0 | 0 | 0 | 0 | 10 | 8 | 7 | 7 | 0 |
| | 31.25 | 0 | 0 | 0 | 0 | 0 | 0 | 7 | 7 | 6 | 6 | 0 |
| Reference Compound (XXIII) | 125 | 0 | 0 | 0 | 0 | 0 | 0 | 0 | 0 | 0 | 0 | 0 |
| | 62.5 | 0 | 0 | 0 | 0 | 0 | 0 | 0 | 0 | 0 | 0 | 0 |
| | 31.25 | 0 | 0 | 0 | 0 | 0 | 0 | 0 | 0 | 0 | 0 | 0 |
| Reference Compound (XXIV) | 125 | 0 | 0 | 0 | 0 | 0 | 0 | 0 | 0 | 0 | 0 | 0 |
| | 62.5 | 0 | 0 | 0 | 0 | 0 | 0 | 0 | 0 | 0 | 0 | 0 |
| | 31.25 | 0 | 0 | 0 | 0 | 0 | 0 | 0 | 0 | 0 | 0 | 0 |

TABLE 18

(Test 4-2)

| Compound No. | Concentration (ppm) | Ric. | Mai. | Wh. | So. | Cot. | Ra. | B.G. | Cr.G. | D.G. | J.G. | G.F. |
|---|---|---|---|---|---|---|---|---|---|---|---|---|
| Compound No. 2-1 | 125 | 7 | 8 | 0 | 0 | 0 | 0 | 10 | 10 | 10 | 10 | 0 |
| | 62.5 | 1 | 3 | 0 | 0 | 0 | 0 | 10 | 10 | 10 | 10 | 0 |
| Compound No. 2-2 | 125 | 7 | 8 | 0 | 0 | 0 | 0 | 10 | 10 | 10 | 10 | 0 |
| | 62.5 | 2 | 3 | 0 | 0 | 0 | 0 | 10 | 10 | 10 | 10 | 0 |
| Compound No. 2-3 | 125 | 7 | 7 | 0 | 0 | 0 | 0 | 10 | 10 | 10 | 10 | 0 |
| | 62.5 | 2 | 2 | 0 | 0 | 0 | 0 | 10 | 10 | 10 | 10 | 0 |
| Compound No. 2-4 | 125 | 6 | 3 | 0 | 0 | 0 | 0 | 10 | 10 | 10 | 10 | 0 |
| | 62.5 | 0 | 0 | 0 | 0 | 0 | 0 | 10 | 10 | 10 | 10 | 0 |
| Compound No. 2-5 | 125 | 5 | 2 | 0 | 0 | 0 | 0 | 10 | 10 | 10 | 10 | 0 |
| | 62.5 | 0 | 0 | 0 | 0 | 0 | 0 | 10 | 10 | 10 | 10 | 0 |
| Compound No. 2-6 | 125 | 5 | 2 | 0 | 0 | 0 | 0 | 10 | 10 | 10 | 10 | 0 |
| | 62.5 | 0 | 0 | 0 | 0 | 0 | 0 | 10 | 10 | 10 | 10 | 0 |

TABLE 19

(Test 4-3)

| Compound No. | Concentration (ppm) | Ric. | Mai. | Wh. | So. | Cot. | Ra. | B.G. | Cr.G. | D.G. | J.G. |
|---|---|---|---|---|---|---|---|---|---|---|---|
| Compound No. 8-1 | 125 | 3 | 2 | 0 | 0 | 0 | 0 | 10 | 10 | 10 | 10 |
| | 62.5 | 0 | 0 | 0 | 0 | 0 | 0 | 10 | 10 | 10 | 10 |
| | 31.25 | 0 | 0 | 0 | 0 | 0 | 0 | 10 | 10 | 10 | 10 |
| Compound No. 8-2 | 125 | 2 | 1 | 0 | 0 | 0 | 0 | 10 | 10 | 10 | 10 |
| | 62.5 | 0 | 0 | 0 | 0 | 0 | 0 | 10 | 10 | 10 | 10 |
| | 31.25 | 0 | 0 | 0 | 0 | 0 | 0 | 10 | 10 | 10 | 10 |
| Reference Compound (XVIII) | 125 | 5 | 4 | 3 | 0 | 0 | 0 | 7 | 4 | 6 | 1 |
| | 62.5 | 2 | 2 | 2 | 0 | 0 | 0 | 2 | 0 | 3 | 0 |
| | 31.25 | 0 | 0 | 1 | 0 | 0 | 0 | 0 | 0 | 0 | 0 |
| Reference Compound (XIX) | 125 | 7 | 2 | 3 | 0 | 0 | 0 | 7 | 6 | 5 | 4 |
| | 62.5 | 3 | 0 | 1 | 0 | 0 | 0 | 3 | 4 | 3 | 0 |
| | 31.25 | 1 | 0 | 0 | 0 | 0 | 0 | 0 | 0 | 0 | 0 |
| Reference Compound (XX) | 125 | 4 | 2 | 4 | 0 | 0 | 0 | 6 | 5 | 5 | 4 |
| | 62.5 | 1 | 0 | 2 | 0 | 0 | 0 | 2 | 2 | 1 | 1 |
| | 31.25 | 0 | 0 | 0 | 0 | 0 | 0 | 0 | 0 | 0 | 0 |
| Reference Compound (XXI) | 125 | 5 | 3 | 3 | 0 | 0 | 0 | 6 | 6 | 5 | 5 |
| | 62.5 | 2 | 1 | 1 | 0 | 0 | 0 | 4 | 2 | 4 | 2 |
| | 31.25 | 0 | 0 | 0 | 0 | 0 | 0 | 1 | 0 | 0 | 1 |

TABLE 19-continued (Test 4-3)

| Compound No. | Concentration (ppm) | Ric. | Mai. | Wh. | So. | Cot. | Ra. | B.G. | Cr.G. | D.G. | J.G. |
|---|---|---|---|---|---|---|---|---|---|---|---|
| Reference | 125 | 4 | 2 | 3 | 0 | 0 | 0 | 7 | 6 | 6 | 6 |
| Compound (XXII) | 62.5 | 1 | 1 | 0 | 0 | 0 | 0 | 4 | 3 | 4 | 2 |
|  | 31.25 | 0 | 0 | 0 | 0 | 0 | 0 | 0 | 0 | 1 | 1 |

What is claimed is:

1. Phenoxyphenoxy unsaturated derivative having the formula

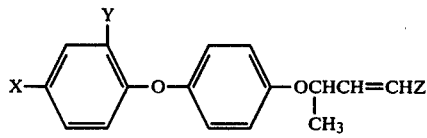
(I)

wherein X represents a halogen atom or CF$_3$; Y represents a hydrogen atom or a halogen atom; and Z represents —COOR, —COR", —CH$_2$OH or —CH$_2$OR"' and R represents cyanoethyl, dialkylaminoethyl, alkoxyalkyl, benzyl, dialkylbenzyl, alkylbenzyl, halobenzyl, pyridinomethyl, furfuryl, cycloalkyl, methylcycloalkyl, phenyl, halophenyl, methyl phenyl, alkoxy alkyleneoxy alkyl, methoxymethylbutyl group, a metal atom, amino, alkylamino or arylamino group; and when X is a halogen atom, R can be an alkyl, haloalkyl, alkenyl, haloalkenyl, alkynyl or hydrogen atom group; and R" represents a hydrogen atom, amino, alkylamino, dialkylamino, phenylamino or phenylamino group which may be substituted by halo or alkyl group, and R"' represents an acetyl, chloroacetyl, benzoyl, ethoxycarbonyl, methylcarbamoyl or phenylcarbamoyl group.

2. Phenoxyphenoxy unsaturated derivatives according to claim 1 which are phenoxyphenoxy unsaturated derivatives having the formula

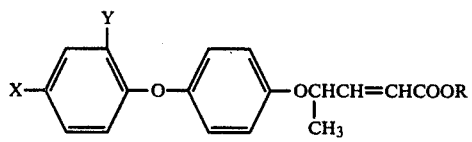

wherein X, Y and R are defined above.

3. Phenoxyphenoxy unsaturated derivatives according to claim 1 which are phenoxyphenoxy unsaturated derivatives having the formula

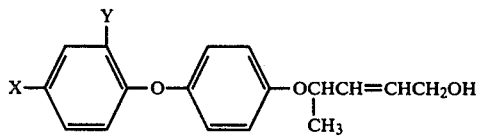

wherein X and Y are defined above.

4. Phenoxyphenoxy unsaturated derivatives according to claim 1 which are phenoxyphenoxy unsaturated derivatives having the formula

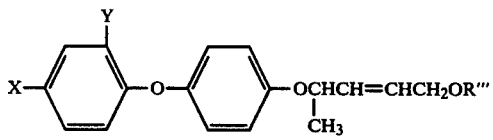

wherein X, Y and R"' are defined above.

5. A herbicidal composition which comprises a phenoxyphenoxy unsaturated derivative having the formula

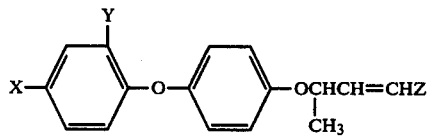
(I)

wherein X represents a halogen atom or CF$_3$; Y represents a hydrogen atom or a halogen atom; and Z represents —COOR, —COR", —COOH, —CH$_2$OH or —CH$_2$OR"' and R represents cyanoethyl, dialkylaminoethyl, alkoxyalkyl, benzyl, dialkylbenzyl, alkylbenzyl, halobenzyl, pyridinomethyl, furfuryl, cycloalkyl, methylcyloalkyl, phenyl, halophenyl, methyl phenyl, alkoxy alkyleneoxy alkyl, methoxymethylbutyl group, a metal atom, amino, alkylamino or arylamino group; and when X is a halogen atom, R can be an alkyl, haloalkyl, alkenyl, haloalkenyl, alkynyl or hydrogen atom group; and R" represents, amino, alkylamino, dialkylamino, phenylamino or phenylamino group which may be substituted by halo or alkyl group, and R"' represents an acetyl, chloroacetyl, benzoyl, ethoxycarbonyl, methylcarbamoyl or phenylcarbamoyl group.

6. A herbicidal composition according to claim 5 wherein the compound (I) is a phenoxyphenoxy unsaturated derivative having the formula

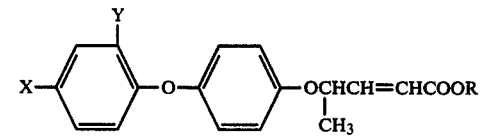

7. A herbicidal composition according to claim 5 wherein the compound (I) is a phenoxyphenoxy unsaturated derivative having the formula

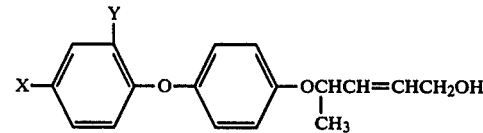

8. A method of treating plants with a herbicide, comprising:
   applying a herbicidally effective amount of the herbicidal composition of claim 5 to the soil or the foliage of plants.

9. A method of treating plants with a herbicide, comprising:
   applying an amount of the composition of claim 5 to the soil such that from 0.01 to 10 kg of the active ingredient of said composition is applied per 1 ha. of soil 10. A method of treating plants with a herbicide, comprising:
   applying the composition of claim 5 diluted to an active ingredient concentration of 10 to 10,000 ppm to the foilage of plants.

* * * * *